United States Patent
Melloni et al.

(10) Patent No.: US 9,474,739 B2
(45) Date of Patent: *Oct. 25, 2016

(54) SUBSTITUTED 2-[2-(PHENYL) ETHYLAMINO] ALKANEAMIDE DERIVATIVES AND THEIR USE AS SODIUM AND/OR CALCIUM CHANNEL MODULATORS

(71) Applicant: NEWRON PHARMACEUTICALS S.P.A., Bresso (IT)

(72) Inventors: Piero Melloni, Bresso (IT); Alessandra Restivo, Milan (IT); Emanuela Izzo, Milan (IT); Simona Francisconi, Milan (IT); Elena Colombo, Inverigo (IT); Cibele Sabido-David, Milan (IT)

(73) Assignee: NEWRON PHARMACEUTICALS S.P.A., Bresso (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/615,227

(22) Filed: Feb. 5, 2015

(65) Prior Publication Data

US 2015/0157601 A1 Jun. 11, 2015

Related U.S. Application Data

(60) Division of application No. 13/794,377, filed on Mar. 11, 2013, which is a continuation of application No. 12/663,926, filed as application No. PCT/EP2008/003848 on May 14, 2008, now Pat. No. 8,519,000.

(30) Foreign Application Priority Data

Jun. 15, 2007 (EP) .................................... 07011766

(51) Int. Cl.
| | | |
|---|---|---|
| *A61K 31/165* | (2006.01) | |
| *A61K 31/137* | (2006.01) | |
| *A61P 1/00* | (2006.01) | |
| *A61K 31/381* | (2006.01) | |
| *C07C 237/08* | (2006.01) | |
| *C07C 317/28* | (2006.01) | |
| *C07C 323/25* | (2006.01) | |
| *C07C 327/42* | (2006.01) | |
| *C07D 295/182* | (2006.01) | |
| *A61K 31/40* | (2006.01) | |
| *A61K 31/4515* | (2006.01) | |
| *A61K 31/519* | (2006.01) | |

(Continued)

(52) U.S. Cl.
CPC ........... *A61K 31/381* (2013.01); *A61K 31/137* (2013.01); *A61K 31/165* (2013.01); *A61K 31/40* (2013.01); *A61K 31/4515* (2013.01); *A61K 31/519* (2013.01); *A61K 31/5513* (2013.01); *C07C 237/06* (2013.01); *C07C 237/08* (2013.01); *C07C 237/20* (2013.01); *C07C 317/28* (2013.01); *C07C 321/26* (2013.01); *C07C 323/25* (2013.01); *C07C 327/42* (2013.01); *C07C 327/44* (2013.01); *C07D 207/16* (2013.01); *C07D 295/182* (2013.01); *C07D 333/20* (2013.01)

(58) Field of Classification Search
CPC ........................ A61K 31/165; A61K 31/137
See application file for complete search history.

(56) References Cited

U.S. PATENT DOCUMENTS

| 3,759,979 A | 9/1973 | Beregi et al. |
| 5,051,403 A | 9/1991 | Miljanich et al. |

(Continued)

FOREIGN PATENT DOCUMENTS

| DE | 2006978 | 9/1970 |
| EP | 1870097 | 12/2007 |

(Continued)

OTHER PUBLICATIONS

Alzheimer, C., 2002, "Na+ channels and Ca2+ channels of the cell membrane as targets of neuroprotecti ve substances," Advances in Experimental Medicine and Biology 513:161-181.

(Continued)

*Primary Examiner* — Sahar Javanmard
(74) *Attorney, Agent, or Firm* — Silvia Salvadori, P.C.; Silvia Salvadori

(57) ABSTRACT

Substituted 2-[2-(phenyl)ethylamino]alkaneamide derivatives of formula (I)

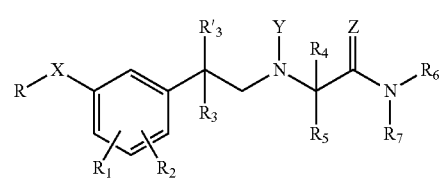

wherein
X, Y, Z, R, $R_1$, $R_2$, $R_3$, $R'_3$ $R_4$, $R_5$, $R_6$, $R_7$ have the meanings defined in the specification and pharmaceutically acceptable salts thereof, pharmaceutical compositions containing them as active ingredient and their use as sodium and/or calcium channel modulators useful in preventing, alleviating and curing a wide range of pathologies, including, but not limited to, neurological, cognitive, psychiatric, inflammatory, urogenital and gastrointestinal diseases, where the above mechanisms have been described as playing a pathological role.

8 Claims, 2 Drawing Sheets

(51) Int. Cl.
*A61K 31/5513* (2006.01)
*C07C 237/06* (2006.01)
*C07D 207/16* (2006.01)
*C07D 333/20* (2006.01)
*C07C 237/20* (2006.01)
*C07C 321/26* (2006.01)
*C07C 327/44* (2006.01)

(56) References Cited

U.S. PATENT DOCUMENTS

| | | |
|---|---|---|
| 5,236,957 A | 8/1993 | Dostert et al. |
| 5,391,577 A | 2/1995 | Dostert et al. |
| 5,502,079 A | 3/1996 | Dostert et al. |
| 5,587,454 A | 12/1996 | Justice et al. |
| 5,863,952 A | 1/1999 | Orlek et al. |
| 5,945,454 A | 8/1999 | Pevarello et al. |
| 6,011,035 A | 1/2000 | Snutch et al. |
| 6,117,841 A | 9/2000 | Hu et al. |
| 6,306,903 B1 | 10/2001 | Pevarello et al. |
| 6,362,174 B1 | 3/2002 | Rafferty et al. |
| 6,420,383 B1 | 7/2002 | Henry |
| 6,458,781 B1 | 10/2002 | Connor et al. |
| 6,472,530 B1 | 10/2002 | Dodd et al. |
| 6,521,647 B2 | 2/2003 | Foster |
| 2007/0093495 A1 | 4/2007 | Ruggero et al. |
| 2007/0203182 A1 | 8/2007 | Besana et al. |

FOREIGN PATENT DOCUMENTS

| | | |
|---|---|---|
| GB | 586645 | 3/1947 |
| WO | 9014334 | 11/1990 |
| WO | 9710210 | 3/1997 |
| WO | 9835957 | 8/1998 |
| WO | 9914199 | 3/1999 |
| WO | 9935125 | 7/1999 |
| WO | 0174779 | 10/2001 |
| WO | 03018561 | 3/2003 |
| WO | 03020273 | 3/2003 |
| WO | 03057219 | 7/2003 |
| WO | 2004062655 | 7/2004 |
| WO | 2004087125 | 10/2004 |
| WO | 2004089353 | 10/2004 |
| WO | 2005018627 | 3/2005 |
| WO | 2005070405 | 8/2005 |
| WO | 2005102300 | 11/2005 |
| WO | 2006027052 | 3/2006 |
| WO | 2007071311 | 6/2007 |

OTHER PUBLICATIONS

Arban et al., 2005, "Evaluation of the effects oflamotrigine, valproate and carbamazepine in a rodent model of mania," Behavioural Brain Research 158(1):123-132.
Baumann, P., 1996, "Pharmacokinetic-pharmacodynamic relationship of the selective serotonin reuptake inhibitors," Clinical Pharmacokinetics 31(6):444-469.
Bizot et al., 2005, "Chronic treatment with sulbutiamine improves memory in an object recognition task and reduces some amnesic effects of dizocilpine in a spatial delayed-non-match-to-sample task," Progress in Neuro-Psychopharmacology & Biological Psychiatry 29(6):928-935.
Bortolato et al., 2007, "Activation ofGABA(B) receptors reverses spontaneous gating deficits injuvenile DBA/2J mice," Psychopharmacology 194(3):361-369.
Bowersox & Luther, 1998, "Pharmacotherapeutic potential of omegaconotoxin MVIIA (SNX-111), an N-type neuronal calcium channel blocker found in the venom ofConus magus," Toxicon: Official Journal of the International Society on Toxinology 36(11):1651-1658.
Catterall, W.A., 1987, "Common modes of drug action on Na+ channels: Local anesthetics, antiarrhythmics and anticonvulsants," Trends Pharmacol. Sci. 8:57-65.
Chaplan et al., 1994, "Quantitative assessment of tactile allodynia in the rat paw," Journal of Neuroscience Methods 53(1):55-63.
Cizkova et al., 2002, "Localization ofN-type Ca2+ channels in the rat spinal cord following chronic constrictive nerve injury," Experimental Brain Research Experimentelle Hirnforschung. Experimentation Cerebrate 147(4):456-463.
Cooper, A. J., 1989, "Tyra.mine and irreversible monoamine oxidase inhibitors in clinical practice," The British Journal of Psychiatry. Supplement (6):38-45.
Deschaux et al., 1997, "Apamin improves learning in an object recognition task in rats," Neuroscience Letters 222(3):159-162.
Diaz & Dickenson, 1997, "Blockade of spinal N- and P-type, but not L-type, calcium channels inhibits the excitability of rat dorsal horn neurones produced by subcutaneous formalin inflammation," Pain 69(1-2):93-100.
Dixon, W.J., 1965, "The Up-and-Down Method for Small Samples," Journal of the American Statistical Association 60:967-978.
Ennaceur et al., 1989, "A new one-trial test for neurobiological studies of memory in rats. II: Effects of piracetam and pramiracetam," Behavioural Brain Research 33(2):197-207.
Friese et al., 1997, "Reversal by kappa-agonists of peritoneal irritation-induced ileus and visceral pain in rats," Life Sciences 60(9):625-634.
Gessa et al., 1995, "Sleep deprivation in the rat: an animal model of mania," European Neuropsychopharmacology: The Journal of the European College of Neuropsychopharmacology Supplemental 5:89-93.
Ghidini et al., 2006, "Synthesis and anticonvulsant activity ofa class oft-amino 3-hydroxypropanamide and 2-aminoacetamide derivatives," Bioorganic & Medicinal Chemistry 14(10):3263-3274.
Greco et al., 2005, "Phencyclidine-induced impairment in attention and response control depends on the background genotype of mice: reversal by the mGLU(2/3) receptor agonist L Y379268," Psychopharmacology 179(1 ):68-76.
Hamill et al., 1981, "Improved patch-clamp techniques for high-resolution current recording from cells and cell-free membrane patches," Pjlugers Archiv: European Journal of Physiology 391(2):85-100.
Hatakeyama et al., 2001, "Differential nociceptive responses in mice lacking the a 18 subunit ofN-type Ca2+channels," Neuroreport 12:2423-2427.
International Search Report from PCT/EP08/003848 dated Nov. 14, 2008.
Javitt & Zukin, 1991, "Recent advances in the phencyclidine model of schizophrenia," The American Journal of Psychiatry 148(10): 1301-1308.
Jouvet et al., 1964, Journal of Physiology (Paris) 56:381.
Kim et al., 2001, "Altered nociceptive response in mice deficient in the alB subunit of the voltage-dependent calcium channel," Molecular and Cellular Neurosciences 18(2):235-245.
Kim & Chung, 1992, "An experimental model for peripheral neuropathy produced by segmental spinal nerve ligation in the rat," Pain 50(3):355-363.
Koob et al., 1998, "Neuroscience of addiction," Neuron 21(3):467-476.
Matthews & Dickenson, 2001, "Effects of spinally delivered N- and P-type voltage-dependent calcium channel antagonists on dorsal horn neuronal responses in a rat model of neuropathy," Pain 92(1-2):235-246.
Morris, R. G. M., 1981, "Spatial localization does not require the presence oflocal cues," Learn. Motiv. 12:239-260.
Nebe et al., 1998, "Spinal application of omega-conotoxin GVIA, an N-type calcium channel antagonist, attenuates enhancement of dorsal spinal neuronal responses caused by intra-articular injection of mustard oil in the rat," &perimental Brain Research. &perimentelle Hirnforschung. &perimentation Cerebrate 120(1):61-69.
Porsolt et al. 1977, "Behavioral despair in mice: a primary screening test for antidepressants," Archives Internationales De Pharmacodynamie Et De Therapie 229(2): 327-336.

(56) References Cited

OTHER PUBLICATIONS

Puma & Bizot, 1998, "Intraseptal infusions ofa low dose of AP5, a NMDA receptor antagonist, improves memory in an object recognition task in rats," Neuroscience Letters 248(3):183-186.

Robinson & Berridge, 1993, "The neural basis of drug craving: an incentivesensitization theory of addiction," Brain Research. Brain Research Reviews 18(3):247-291.

Rosland et al., 1990, "The formalin test in mice: effect of formalin concentration," Pain 42(2):235-242.

Rushton & Steinberg, 1966, "Combined effects of chlordiazepoxide and dexamphetamine on activity ofrats in an unfamiliar environment," Nature 211(5055):1312-1313.

Saegusa et al., 2001, "Suppression of inflammatory and neuropathic pain symptoms in mice lacking the N-type Ca2+ channel," The EMBO Journal 20(10):2349-2356.

Steru et al., 1987, "The automated Tail Suspension Test: a computerized device which differentiates psychotropic drugs," Progress in Neuro-Psychopharmacology & Biological Psychiatry 11(6):659-671.

Steru et al., 1985, "The tail suspension test: a new method for screening antidepressants in mice," Psychopharmacology 85(3):367-370.

Tjolsen et al., 1992, "The formalin test: an evaluation of the method," Pain 51(1):5-17.

Vanegas & Schaible, 2000, "Effects of antagonists to high-threshold calcium channels upon spinal mechanisms of pain, hyperalgesia and allodynia," Pain 85(1-2):9-18.

Volz & Gleiter, 1998, "Monoamine oxidase inhibitors. A perspective on their use in the elderly," Drugs & Aging 13(5):341-355.

Wood et al., 1990, "Novel cell lines display properties ofnociceptive sensory neurons," Proceedings. Biological Sciences I The Royal Society 241(1302):187-194.

Yamada & Richelson, 1996, "Pharmacology of antidepressants in the elderly," Handbook of pharmacology of aging.

SUBSTITUTED 2-[2-(PHENYL) ETHYLAMINO] ALKANEAMIDE DERIVATIVES AND THEIR USE AS SODIUM AND/OR CALCIUM CHANNEL MODULATORS

This application is a divisional of U.S. patent application Ser. No. 13/794,377, filed on Mar. 11, 2013, which is a continuation of U.S. patent application Ser. No. 12/663,926, now U.S. Pat. No. 8,519,000, filed on Apr. 30, 2010, which a U.S. national stage of PCT/EP2008/003848 filed on May 14, 2008 which claims priority to and the benefit of EP 07022766.8 filed Jun. 15, 2007, the contents of which are incorporated herein by reference in their entireties.

The present invention relates to substituted 2-[2-(phenyl) ethylamino]alkaneamide derivatives, pharmaceutically acceptable salts thereof, pharmaceutical compositions containing them and their use as sodium and/or calcium channel modulators.

The substituted 2-[2-(phenyl)ethylamino]alkaneamide derivatives of the disclosure, are active as sodium and/or calcium channel modulators. Accordingly, they are useful in preventing alleviating and curing a wide range of pathologies, including, but not limited to neurological, cognitive, psychiatric, inflammatory, urogenital and gastrointestinal diseases, where the above mechanisms have been described as playing a pathological role.

The compounds of this invention are substantially free of monoamine oxidase (MAO) inhibitory effect, especially at dosages that are therapeutically effective in preventing, alleviating and/or curing said afflictions.

BACKGROUND OF THE INVENTION

Chemical Background

The GB 586,645 patent describes the synthesis of amino acid derivatives of the following general formula

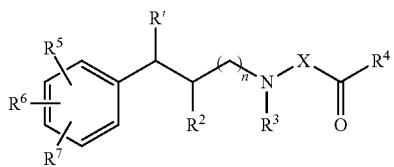

In particular it describes the synthesis of N-hydroxyalkylamides having stimulating uterine smooth muscle properties.

The patent application WO 90/14334 describes mono-substituted N-phenylalkyl alpha-amino carboxamide derivatives of the following general formula

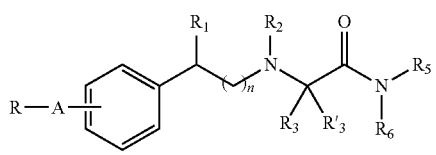

wherein
R is a $(C_1-C_8)$alkyl, $(C_3-C_8)$cycloalkyl, furyl, thienyl, pyridyl or a phenyl ring optionally substituted by 1 to 4 substituents independently selected from halo, $(C_1-C_6)$alkyl, $(C_1-C_6)$alkoxy and trifluoromethyl; A is a $—(CH_2)_m—$ or $—(CH_2)p-X—(CH_2)q-$ group wherein m is an integer of 1 to 4, one of p and q is zero and the other is zero or an integer of 1 to 4, X is $—O—$, $—S—$ or $—NR_4—$ in which $R_4$ is hydrogen or $(C_1-C_4)$alkyl; n is 0 or 1; each of $R_1$ and $R_2$ independently is hydrogen or $(C_1-C_4)$alkyl; $R_3$ is hydrogen, $(C_1-C_4)$alkyl optionally substituted by hydroxy or phenyl optionally substituted as above; $R_3'$ is hydrogen or $R_3$ and $R_3'$ taken together form a $(C_3-C_6)$cycloalkyl ring; each of $R_5$ and $R_6$ independently is hydrogen or $(C_1-C_6)$ alkyl, with the proviso that when R is $(C_1-C_8)$alkyl, then A is a $—(CH_2)_p—X—(CH_2)_q—$ group in which p and q are both zero and X is $—O—$, $—S—$ or $—NR_4—$, in which $R_4$ is hydrogen or $C_1-C_4$ alkyl for use as anti-epileptic, anti-Parkinson, neuroprotective, anti-depressant, anti-spastic and/or hypnotic agents.

None of derivatives synthesized in our patent application is specifically disclosed and prepared in WO 90/14334.

In other patent applications, selected compounds falling in WO 90/14334 general formula, are claimed for use in compositions having other activities, specifically:
WO 99/35125 Alpha-aminoamide derivatives useful as analgesic agents
WO 03/020273 Pharmaceutical composition comprising gabapentin or analogue thereof and an alpha aminoamide and its analgesic use
WO 04/062655 Alpha-aminoamide derivatives useful as antimigraine agents
WO 05/018627 Alpha-aminoamide derivatives useful as anti-inflammatory agents
WO 05/070405 Alpha-aminoamide derivatives useful in the treatment of lower urinary tract disorders
WO 05/102300 Alpha-aminoamide derivatives useful in the treatment of Restless Legs Syndrome and additive disorders
WO 06/027052 Use of (halobenzyloxy) benzylamino-propanamides for the manufacture of medicaments active as sodium and/or calcium channel selective modulators
EP Appl. No 06012352.8 α-Aminoamide Derivatives Useful in the Treatment of Cognitive Disorders.

In the patent application WO 98/35957 amide derivatives of the following general formula are described

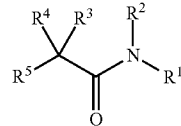

and are claimed to be useful against obesity and eating disorders.

None of the compounds synthesized in our patent application has been actually synthesized or specifically listed in this WO 98/35957.

In WO 2004/087125, compounds of the following general formula are described:

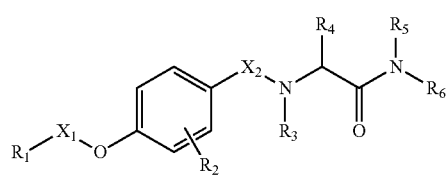

A sodium channels blocking mechanism and many pharmacological activities are claimed, in particular anti-pain and anti bladder dysfunction activities.

It must be underlined that when $X_2$ is an alkylene, it cannot be —$CH_2$—$CH_2$— but only —$CH_2$—, so none of the 2-[2-(phenyl)ethylamino]alkaneamide derivatives of this application falls within the general formula reported above.

Eleonora Ghidini et al., in Bioorganic & Medicinal Chemistry 2006, 14, 3263-3274 describe compounds of the following general formula:

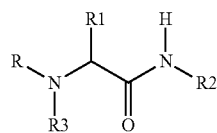

These compounds have been tested for an anticonvulsant activity.

None of the compounds disclosed and synthesized in this patent application falls within the general formula described above.

The co-pending application PCT/EP 2006/011443 (WO 2007/071311) filed on Nov. 29, 2006, refers to 2-phenylethylamino derivatives of the following general formula:

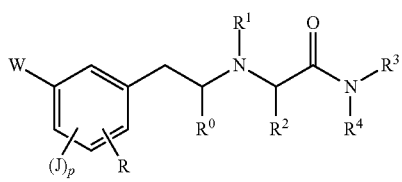

None of the compounds claimed in this application falls within the PCT/EP 2006/011443 (WO 2007/071311).

Biological Background

Sodium channels play an important role in the neuronal network by transmitting electrical impulses rapidly throughout cells and cell networks, thereby coordinating higher processes ranging from locomotion to cognition. These channels are large transmembrane proteins, which are able to switch between different states to enable selective permeability for sodium ions. For this process an action potential is needed to depolarize the membrane, and hence these channels are voltage-gated. In the past few years a much better understanding of sodium channels and drugs interacting with them has been developed.

Voltage-gated sodium channels were originally classified based on their sensitivity to tetrodotoxin, from low nanomolar (Tetrodotoxin sensitive, TTXs) to high micromolar (Tetrodotoxin resistant, TTXr). So far, 9 different sodium channel a subunits have been identified and classified as Nav1.1 to Nav1.9.

Nav1.1 to Nav1.4, Nav1.6 and Nav1.7 are TTXs, whereas Nav1.5, Nav1.8 and Nav.1.9 are TTXr, with different degrees of sensitivity. Nav1.1 to Nav1.3 and Nav1.6, are primarily expressed in the CNS, whereas Nav1.4 and Nav1.5 are mainly expressed in muscle (skeletal and heart respectively) and Nav1.7, Nav1.8 and Nav1.9 are predominantly expressed in DRG sensory neurons.

It has become clear that a number of drugs having an unknown mechanism of action actually act by modulating sodium channel conductance, including local anaesthetics, class I antiarrhythmics and anticonvulsants. Neuronal sodium channel blockers have found application with their use in the treatment of epilepsy (phenytoin and carbamazepine), bipolar disorder (lamotrigine), preventing neurodegeneration, and in reducing neuropathic pain. Various anti-epileptic drugs that stabilize neuronal excitability are effective in neuropathic pain (e.g. carbamazepine).

In addition, an increase in sodium channel expression or activity has also been observed in several models of inflammatory pain, suggesting a role of sodium channels in inflammatory pain.

Calcium channels are membrane-spanning, multi-subunit proteins that allow controlled entry of calcium ions into cells from the extracellular fluid. Commonly, calcium channels are voltage dependent and are referred to as voltage-gated calcium channels (VGCC). VGCCs are found throughout the mammalian nervous system, where they regulate the intracellular calcium ions levels that are important for cell viability and function. Intracellular calcium ion concentrations are implicated in a number of vital processes in animals, such as neurotransmitter release, muscle contraction, pacemaker activity and secretion of hormones. All "excitable" cells in animals, such as neurons of the central nervous system (CNS), peripheral nerve cells, and muscle cells, including those of skeletal muscles, cardiac muscles and venous and arterial smooth muscles, have voltage dependent calcium channels.

Calcium channels are a large family with many genetically, physiologically, and pharmacologically distinct subtypes. Based on the biophysical properties of calcium currents recorded from individual neurons, two super-families have been described: High Voltage Activated (HVA) and Low Voltage Activated (LVA) calcium channels. Calcium currents are referred to as L-Type, P-Type, Q-Type, N-Type, and R-Type. This class of calcium currents belong to the HVA super-family, whereas T-Type currents belong to the LVA super family. From their molecular identity, ten distinct calcium channel subtypes have been identified, cloned and expressed and grouped into three families: the Cav1 family (Cav 1.1, 1.2, 1.3, 1.4) is functionally related to the L-type Ca current; the Cav2 family (Cav 2.1, 2.2, 2.3) is functionally related to the P/Q, N, R-type currents and the Cav3 (Cav 3.1, 3.2, 3.3) family is functionally related to the T-type current.

It is believed that calcium channels are relevant in certain disease states. A number of compounds useful in treating various cardiovascular diseases in mammals, including humans, are thought to exert their beneficial effects by modulating functions of voltage dependant calcium channels present in cardiac and/or vascular smooth muscle. Compounds with activity against calcium channels have also been implicated for the treatment of pain. In particular N-type calcium channels (Cav2.2), responsible for the regulation of neurotransmitter release, are thought to play a significant role in nociceptive transmission, both due to their tissue distribution as well as from the results of several pharmacological studies. N-type calcium channels were found up-regulated in the ipsilateral dorsal horn in neuropathic pain models of injury (Cizkova D., et al., Exp. Brain Res. (2002) 147: 456-463). Specific N-type calcium channel blockers were shown to be effective in reducing pain responses in neuropathic pain models (Matthews E. A., Dickenson A. H. Pain (2001) 92: 235-246) in the phase II of the formalin test (Diaz A., Dickenson A. H. Pain (1997) 69: 93-100) and the hyperalgesia initiated by knee joint inflammation (Nebe J., Vanegas H., Schaible H. G. Exp. Brain Res.

(1998) 120: 61-69). Mutant mice, lacking the N-type calcium channels, were found to have a decreased response to persistent pain as seen by a decrease in pain response during phase II of the formalin test (Kim, et al., Mol. Cell Neurosci. (2001) 18: 235-245; Hatakeyama S., et al., Neuroreport (2001) 12: 2423-2427) as well as to neuropathic pain, assessed by a decrease in mechanical allodynia and thermal hyperalgesia in the spinal nerve ligation model. Interestingly, these mice also showed lower levels of anxiety when compared to wild type (Saegusa H., et al., EMBO J. (2001) 20: 2349-2356). The involvement of N-type calcium channels in pain has been further validated in the clinic by ziconotide, a peptide derived from the venom of the marine snail, Conus Magnus. A limitation in the therapeutic use of this peptide is that it has to be administered intrathecally in humans (Bowersox S. S. and Luther R. Toxicon, (1998) 36: 1651-1658).

All together these findings indicate that compounds with sodium and/or calcium channel blockade have a high therapeutic potential in preventing, alleviating and curing a wide range of pathologies, including neurological, psychiatric, urogenital and gastrointestinal diseases, where the above mechanisms have been described as playing a pathological role.

There are many papers and patents which describe sodium channel and/or calcium channel modulators or antagonists for the treatment or modulation of a plethora of disorders, such as their use as local anaesthetics, antimanic antidepressants, agents for the treatment of unipolar depression, urinary incontinence, diarrhoea, inflammation, epilepsy, neurodegenerative conditions, nerve cell death, neuropathic pain, migraine, acute hyperalgesia and inflammation, renal disease, allergy, asthma, bronchospasm, dysmenorrhea, esophageal spasm, glaucoma, urinary tract disorders, gastrointestinal motility disorders.

A non-exhaustive list of such papers and patents/patent applications describing sodium and/or calcium channels blockers and uses thereof includes the references shown below:

C. Alzheimer describes in Adv. Exp. Med. Biol. 2002, 513, 161-181, sodium and calcium channels as targets of neuroprotective substances.

Vanegas e Schaible (Pain 2000, 85, 9-18) discuss effects of antagonists of calcium channels upon spinal mechanisms of pain, hyperalgesia and allodynia.

WO 03/057219 relates to sodium channel blockers useful as agents for treating or modulating a central nervous system disorder, such as neuropathic pain, inflammatory pain, inflammation-related pain or epilepsy.

WO99/14199 discloses substituted 1,2,3,4,5,6-hexahydro-2,6-methano-3-benzazocines-10-oles as potent sodium channel blockers useful for the treatment of several diseases, such as stroke, neurodegenerative disorders, Alzheimer's Disease, Parkinson's Disease and cardiovascular disorders.

WO01/74779 discloses new aminopyridine sodium channel blockers and their use as anticonvulsants, local anaesthetics, as antiarrhythmics, for the treatment or prevention of neurodegenerative conditions, such as amyotrophic lateral sclerosis (ALS), for the treatment or prevention of both, acute or chronic pain, and for the treatment or prevention of diabetic neuropathy.

WO04/087125 discloses amino acid derivatives as inhibitors of mammalian sodium channels, useful in the treatment of chronic and acute pain, tinnitus, bowel disorders, bladder dysfunction and demyelinating diseases.

U.S. Pat. No. 5,051,403 relates to a method of reducing neuronal damage associated with an ischemic condition, such as stroke, by administration of binding/inhibitory omega-conotoxin peptide wherein the peptide is characterized by specific inhibition of voltage-gated calcium channel currents selectively in neuronal tissues.

U.S. Pat. No. 5,587,454 relates to compositions and methods of producing analgesia particularly in the treatment of pain and neuropathic pain.

U.S. Pat. No. 5,863,952 relates to calcium channel antagonists for the treatment of ischaemic stroke.

U.S. Pat. No. 6,011,035 relates to calcium channel blockers, useful in the treatment of conditions such as stroke and pain.

U.S. Pat. No. 6,117,841 relates to calcium channel blockers and their use in the treatment of stroke, cerebral ischemia, pain, head trauma or epilepsy.

U.S. Pat. No. 6,362,174 relates to N-type calcium channel blockers in the treatment of stroke, cerebral ischemia, pain, epilepsy, and head trauma.

U.S. Pat. No. 6,420,383 and U.S. Pat. No. 6,472,530 relate to novel calcium channel blockers, useful for treating and preventing a number of disorders such as hypersensitivity, allergy, asthma, bronchospasm, dysmenorrhea, esophageal spasm, glaucoma, premature labor, urinary tract disorders, gastrointestinal motility disorders and cardiovascular disorders.

U.S. Pat. No. 6,458,781 relates to compounds that act to block calcium channels and their use to treat stroke, cerebral ischemia, pain, head trauma or epilepsy.

U.S. Pat. No. 6,521,647 relates to the use of calcium channel blockers in the treatment of renal disease in animals, especially chronic renal failure.

WO 97/10210 relates to tricyclic heterocyclic derivatives, and their use in therapy, in particular as calcium channel antagonists, e.g. for the treatment of ischaemia, in particular ischaemic stroke.

WO 03/018561 relates to quinoline compounds as N-type calcium channel antagonists and methods of using such compounds for the treatment or prevention of pain or nociception.

Monoamine oxidase (MAO) is an enzyme present in the outer mitochondrial membrane of neuronal and non-neuronal cells. Two isoforms of MAO exist: MAO-A and MAO-B. MAO enzymes are responsible for the oxidative deamination of endogenous and xenobiotic amines, and have a different substrate preference, inhibitor specificity, and tissue distribution. Serotonin, noradrenaline and adrenaline are preferential substrates for MAO-A, and clorgyline is a selective MAO-A inhibitor; whereas MAO-B prefers β-phenylethylamine as a substrate, and is inhibited by selegiline. Dopamine, tyramine and tryptamine are oxidized by both MAO-A and MAO-B, in particular in human brain dopamine is deaminated by 80% by MAO-B.

MAO inhibition allows endogenous and exogenous substrates to accumulate and may thereby, when almost fully inhibited (>90%), alter the dynamics of regular monoamine transmitters. MAO regulate the concentrations in the brain of the most important neurotransmitters such as noradrenaline, serotonin and dopamine which are related to emotion, anxiety and movement. Thus, it is thought that MAO be closely involved in various psychiatric and neurological disorders such as depression, anxiety and Parkinson's disease (PD).

MAO-A inhibitors are mainly used in psychiatry for the treatment of major, refractory and atypical depression as a consequence of their ability to increase the reduced serotonin and noradrenaline brain levels. More recently, MAO-A inhibitors have been used to treat patients with anxiety disorders such as social phobia, panic disorders, post-traumatic stress disorders and obsessive compulsive disorders.

MAO-B inhibitors are mainly used in neurology for the treatment of PD.

There is also recent evidence and interest in the role of MAO-B in other pathological conditions such as Alzheimer's disease (AD). So far no evidence has been reported on MAO-B involvement in the metabolism of co-transmitters, such as colecystokinin, substance P, somatostatin and neurotensin, which are involved in the modulation of pain sensation. For this reason there is no scientific rationale for the use of MAO-B inhibitors in pain syndromes. Adverse drug reactions during clinical practice with MAO inhibitors have been reported. The first generation of non-selective and irreversible MAO inhibitors, such as tranylcypromine and phenelzine, have serious side effects, including hepatotoxicity, orthostatic hypotension and, most importantly, hypertensive crisis that occurs following the ingestion of foods containing tyramine (Cooper A J.—Tyramine and irreversible monoamine oxidase inhibitors in clinical practice.—*Br J Psych Suppl* 1989: 38-45).

When these non-selective and irreversible MAO inhibitors are used, a strict tyramine-reduced diet must be observed. The pressor sensitivity towards tyramine is normalized 4 weeks after cessation of tranylcypromine therapy and more than 11 weeks after cessation of phenelzine therapy.

Selegiline, an irreversible MAO-B inhibitor, especially when used in combination with levodopa, can cause anorexia/nausea, dry mouth, dyskinesia and orthostatic hypotension in patients with PD, the latter being most problematic (Volz H. P. and Gleiter C. H.—Monoamine oxidase inhibitors. A perspective on their use in the elderly.—*Drugs Aging* 13 (1998), pp. 341-355).

In monotherapy, anorexia/nausea, musculoskeletal injuries, and cardiac arrhythmias occurred more often in patients receiving selegiline compared with those receiving placebo. Apart from these adverse effects, increased rates of elevated serum AST and ALT levels were noted. The most frequently reported adverse effect of moclobemide, a selective and reversible MAO-A inhibitor, are sleep disturbances, increased anxiety, restlessness, and headache.

The combination of selective serotonin reuptake inhibitors (SSRIs) and moclobemide has good efficacy in cases of refractory depression, but has created controversy as to whether toxic side effects, such as serotoninergic syndrome, result from this combination (Baumann P.—Pharmacokinetic-pharmacodynamic relationship of the selective serotonin reuptake inhibitors. *Clin Pharmacokinet* 31 (1996), pp 444-469). Because of cardiac arrhythmias and increased liver enzyme levels, electrocardiogram and laboratory values should be checked regularly.

Many types of physiologic changes that occur with aging affect the pharmacodynamics and pharmacokinetics of MAO inhibitors. Indeed, pharmacokinetic variables in the elderly are markedly different form those in younger patients. These variables including absorption, distribution, metabolism and excretion have to be taken into account to avoid or minimize certain adverse effects and drug-drug interactions. Elderly patients are generally more susceptible than younger patients to side effects, including adverse drug reactions. Hypertensive crisis may occur more frequently in elderly than in younger patients, because cardiovascular systems of the elderly are already compromised by age.

The use of sympathomimetic drugs in combination with MAO inhibitors may also elevate blood pressure. In addition, compared with placebo, phenelzine was associated with a significantly higher incidence of drowsiness, tremor, dyskinesia, diarrhea, micturition difficulties, orthostatic effects, and adverse dermatological effects. It is interesting to note that in the elderly, headache is reported with a higher frequency than in younger patients during treatment with moclobemide (Volz H. P. and Gleiter C. H.—Monoamine oxidase inhibitors. A perspective on their use in the elderly. *Drugs Aging* 13 (1998), pp. 341-355).

MAO inhibitors (preferentially MAO-A, but also non selective MAO-A/MAO-B) are sometimes prescribed for depression. Because of the potential risk of suicide, adverse drug reactions and toxicity due to overdose are important factors to consider when choosing an antidepressant. In addition, when MAO inhibitors are used in high dosage, adverse cardiovascular effects seem to increase considerably; and because MAO selectivity is lost with such high doses, tyramine can induce potentially dangerous hypertensive reactions. Acute overdose with MAO inhibitors causes agitation, hallucinations, hyperpyrexia, hyperreflexia and convulsions. Abnormal blood pressure is also a toxic sign, so that gastric lavage and maintenance of cardiopulmonary function may be required. Overdose of traditional non-selective and irreversible MAO inhibitors are considerably dangerous and sometimes fatal (Yamada and Richelson, 1996. Pharmacology of antidepressants in the elderly. In: David J R, Snyder L., editors. Handbook of pharmacology of aging. Boca Raton: CRC Press 1996).

In the treatment of the afflictions wherein sodium and calcium channels mechanism(s) play(s) a pathological role, the inhibition of MAO enzymes is of no benefit. Moreover MAO inhibitory side effects may impose at least two types of negative limitations:

1) Dietary: eating food with high tyramine content may cause severe, even life threatening increase of systemic blood pressure (the so called "cheese-effect").

2) Pharmacological: as an example, pain is often treated with a combination of drugs such as opioid derivatives and tricyclic antidepressant. With MAO inhibitors such association is dangerous as it may cause the serotoninergic syndrome (agitation, tremors, hallucination, hyperthermia and arrhythmias).

Thus, eliminating or significantly reducing MAO inhibitory activity in medicaments active as sodium and/or calcium channel modulators useful in preventing, alleviating and curing a wide range of pathologies where said mechanism(s) play(s) a pathological role, including neurological, psychiatric, inflammatory, urogenital and gastrointestinal diseases, is an unexpected and substantial therapeutic improvement versus compounds of similar efficacy but with the above mentioned side effects.

Taking into account these findings on MAO inhibitors and, in particular, in view of the lack of evidence on the role of MAO-B in pathological afflictions like pain, migraine, inflammatory, urogenital and gastrointestinal diseases, MAO-B inhibition should not be an essential feature for compounds indicated for the above pathologies. Such compounds would thereby avoid producing possible side effects during chronic and/or long-term treatments.

An advantageous solution to the above described problem would consist in providing medicaments which are "selectively active as sodium and/or calcium modulators" or are useful for the "selective treatment" of afflictions, disorders or diseases wherein the sodium and/or calcium channel mechanism(s) play(s) a pathological role. Selective treatment and selective activity as sodium and/or calcium modulators means that the medicaments when administered to a patient in need thereof in amounts that are effective in the treatment of the above said afflictions wherein the above said mechanism(s) play(s) pathological role do not exhibit any MAO inhibitory activity or exhibit a significantly reduced MAO inhibitory activity, thereby avoiding of side effects due to accumulation of endogenous and exogenous monoamine transmitters.

One primary object of this invention is the use of 2-[2-(phenyl)ethylamino]alkaneamide derivatives for the manufacture of a medicament active as sodium and/or calcium channel modulator for the treatment of pathologies where the above said mechanism(s) play(s) a pathological role, which is a neurological, cognitive, psychiatric, inflammatory, urogenital or gastrointestinal disorder, said medicaments being substantially free from any MAO inhibitory activity or having significantly reduced MAO inhibitory activity and, therefore, having a reduced potential for unwanted side effects. Accordingly, a main object of this invention is to provide 2-[2-(phenyl)ethylamino]alkaneamide derivatives for use as medicaments for treating the above described pathologies, characterized in that said medicaments are substantially free from any MAO inhibitory activity or present a significantly reduced MAO inhibitory activity and, therefore, have a reduced potential for unwanted side effects. Said use provides an improved selective resource for the prevention, alleviation and/or cure of the above said pathological afflictions, in particular, in patients who are particularly sensitive to unwanted side-effects due to MAO inhibitory activity, such as those hereinabove described.

A further aspect of this invention is to provide a method for treating a patient affected by a disorder caused by dysfunctions of voltage-gated sodium and/or calcium channels which comprises the administration to said patient of an effective amount of a 2-[2-(phenyl)ethylamino]alkaneamide derivative.

The above mentioned neurological disorders include pain of both chronic and acute type, in particular neuropathic and inflammatory pain, headaches, migraine, spasms; neurodegenerative disorders such as Alzheimer's disease, Parkinson's disease, epilepsy, restless legs syndrome, stroke and cerebral ischemia; cognitive disorders such as Mild Cognitive Impairment (MCI) and psychiatric disorders including depression, bipolar disorders, mania, schizophrenia, psychoses, anxiety and addiction. The above mentioned inflammatory disorders include inflammatory processes affecting all body systems, e.g. inflammatory processes of the muscle-skeletal system, arthritic conditions, disorders affecting skin and related tissues; disorders of the respiratory system as well as disorders of immune and endocrinological system. A more detailed explanation of all above mentioned pathologies is given hereinafter in the following.

DESCRIPTION OF THE INVENTION

Figure 1:
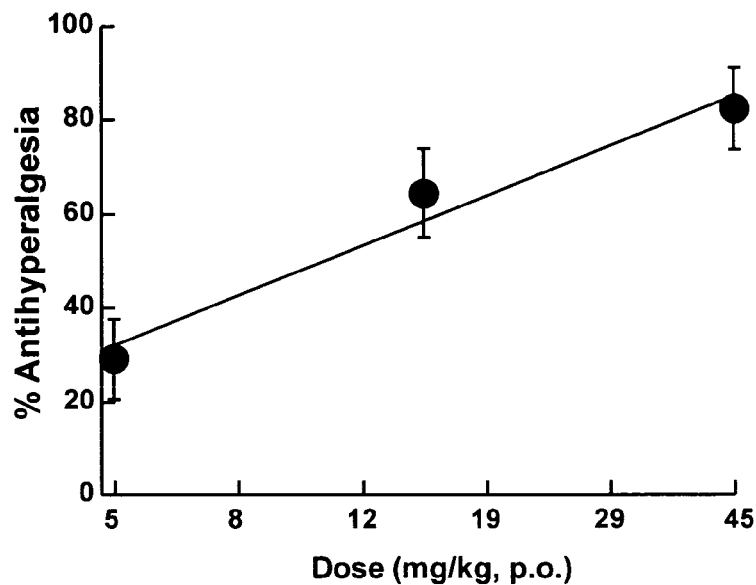
FIG. 1 provides results from testing of a rat spinal nerve ligation model of neuropathic pain further described in Example 17.

The object of this application is a new class of 2-[2-(phenyl)ethylamino]alkaneamide derivatives highly potent as sodium and/or calcium channel modulators and substantially free from any MAO inhibitory activity or having significantly reduced MAO inhibitory activity and, thus, having potentially reduced side effects in preventing, alleviating and curing a wide range of pathologies, including but not limited to neurological, cognitive, psychiatric, inflammatory, urogenital and gastrointestinal diseases where the above mechanisms have been described as playing a pathological role.

In this description and claims, the expression "sodium and/or calcium channel modulator(s)" means compounds able to block sodium and/or calcium currents in a voltage dependent manner.

Therefore, object of the present invention is a compound of general formula (I)

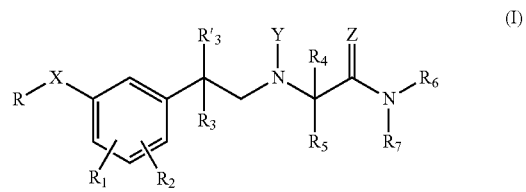

wherein:
X is —O—, —S— or —SO$_2$—;
Y is hydrogen, OH or O(C$_1$-C$_4$)alkyl;
Z is =O or =S;
R is (C$_3$-C$_{10}$)alkyl; ω-trifluoro(C$_3$-C$_{10}$)alkyl;
R$_1$ and R$_2$ are, independently, hydrogen, hydroxy, (C$_1$-C$_8$) alkoxy, (C$_1$-C$_8$) alkylthio, halo, trifluoromethyl or 2,2,2-trifluoroethyl; or one of R$_1$ and R$_2$ is in ortho position to R—X— and, taken together with the same R—X—, represents a

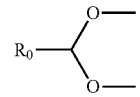

group where R$_0$ is (C$_2$-C$_9$)alkyl;
R$_3$ and R'$_3$ are, independently, hydrogen or (C$_1$-C$_4$)alkyl;
R$_4$ and R$_5$ are, independently, hydrogen, (C$_1$-C$_4$)alkyl; or R$_4$ is hydrogen and R$_5$ is a group selected from —CH$_2$—OH, —CH$_2$—O—(C$_1$-C$_6$)alkyl, —CH(CH$_3$)—OH, —(CH$_2$)$_2$—S—CH$_3$, benzyl and 4-hydroxybenzyl; or R$_4$ and R$_5$, taken together with the adjacent carbon atom, form a (C$_3$-C$_6$)cycloalkyl residue;
R$_6$ and R$_7$ are independently hydrogen or (C$_1$-C$_6$)alkyl; or taken together with the adjacent nitrogen atom form a 5-6 membered monocyclic saturated heterocycle, optionally containing one additional heteroatom chosen among —O—, —S— and —NR$_8$— where R$_8$ is hydrogen or (C$_1$-C$_6$) alkyl;
with the proviso that when X is —S— or —SO$_2$—, then Y is not OH or O(C$_1$-C$_4$) alkyl;

if the case, either as single optical isomer in the isolated form or mixture thereof in any proportion and its pharmaceutically acceptable salts.

Although some of the compounds specifically described in this application are falling within the general formula of WO 90/14334, none of them has been specifically described in said application. None of the compounds defined by the general formula (I) of this application is specifically described or mentioned in WO 90/14334. In fact only few 2-(2-phenyl-ethylamino)alkaneamide derivatives are identified in said prior document which, however, have a benzyloxy, benzylamino or benzyl substituent in the 4-position of the phenyl portion. Moreover, the following selected classes of compounds of formula (I) of this application do not fall within the general formula of WO 90/14334:

a) compounds where X is —$SO_2$—;
b) compounds where Y is OH or $O(C_1-C_4)$alkyl;
c) compounds where Z is =S;
d) compounds where R is $(C_9-C_{10})$alkyl or ω-trifluoro $(C_3-C_{10})$alkyl;
e) compounds where $R_1$ and/or $R_2$ are different from hydrogen;
f) compounds where both $R_3$ and $R'_3$ are different from hydrogen
g) compounds where both $R_4$ and $R_5$ are different from hydrogen, but do not form a $(C_3-C_6)$cycloalkyl residue when taken together with the adjacent carbon atom;
h) compounds where $R_6$ and $R_7$, taken together with the adjacent nitrogen atom form a monocyclic 5-6 membered saturated heterocycle, optionally containing one additional heteroatom chosen among —O—, —S— and —$NR_8$—, where $R_8$ is hydrogen or $(C_1-C_6)$ alkyl.

The term "alkyl" used in this description and claims, where no otherwise specified, identifies a straight or branched alkyl radical; examples of said radicals or moieties include: methyl, ethyl, propyl, isopropyl, butyl, isobutyl, pentyl, isopentyl, hexyl, heptyl, octyl, nonyl, decyl and their isomers.

The term "alkoxy" used in this description and claims identifies a straight or branched alkoxy radical; examples of said radicals include: methoxy, ethoxy, propoxy, isopropoxy, butoxy, isobutoxy, tert-butoxy, pentyloxy, isopentyloxy, hexyloxy, isohexyloxy, heptyloxy, octyloxy and their isomers.

The term "$(C_3-C_6)$cycloalkyl" identifies a cycloaliphatic ring; examples of said rings include: cyclopropyl, cyclobutyl, cyclopentyl and cyclohexyl.

The term "halo" means an halogen atom radical such as fluoro, chloro, bromo and iodo. Examples of a monocyclic 5 or 6 membered saturated heterocycles, optionally containing one additional heteroatom, chosen among —O—, —S— or —$NR_8$—, where $R_8$ is hydrogen or $(C_1-C_6)$ alkyl are, for instance, pyrrolidine, pyrazolidine, imidazolidine, oxazolidine, isoxazolidine, piperidine, piperazine, N-methylpiperazine, morpholine and thiomorpholine. When the compounds of this invention contain one or more asymmetric carbon atoms and, therefore, they can exist as single optical isomers or a mixture thereof, the invention includes within its scope all the possible single optical isomers, (e.g. enantiomers, diastereoisomers) of said compounds in the isolated form and the mixtures thereof in any proportion, including racemic mixtures.

Examples of pharmaceutically acceptable salts of the compounds of formula (I) are salts with organic and inorganic acids such as hydrochloric, hydrobromic, hydroiodic, nitric, sulfuric, phosphoric, acetic, propionic, tartaric, fumaric, citric, benzoic, succinic, cinnamic, mandelic, salicylic, glycolic, lactic, oxalic, malic, maleic, malonic, fumaric, tartaric, p-toluenesulfonic, methanesulfonic, glutaric acid and other acids which, for instance, can be found in: P. Heinrich Stahl, Camille G. Wermuth "Handbook of pharmaceutical salts: properties, selection and use", WILEY-VCH, 2002.

The compounds of formula (I) are active as sodium and/or calcium channel modulators and therefore, are useful in preventing, alleviating and curing a wide range of pathologies, including but not limited to neurological, cognitive, psychiatric, inflammatory, urologic, and gastrointestinal diseases, where the above mechanisms have been described as playing a pathological role.

Preferred compounds of formula (I) are the compounds wherein:

X is —O—, —S—;
Y is hydrogen, OH or $O(C_1-C_3)$alkyl;
Z is =O or =S;
$R_1$ and $R_2$ are, independently, hydrogen, $(C_1-C_4)$alkoxy, halo, trifluoromethyl or 2,2,2-trifluoroethyl; or one of $R_1$ and $R_2$ is in ortho position to R—X— and, taken together with the same R—X—, represent a

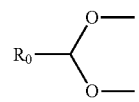

group where $R_0$ is $(C_2-C_5)$alkyl;
$R_3$ and $R'_3$ are, independently, hydrogen or $(C_1-C_3)$alkyl;
$R_4$ and $R_5$ are, independently, hydrogen or $(C_1-C_4)$alkyl; or $R_4$ is hydrogen and $R_5$ is a group selected from —$CH_2$—OH, —$CH_2$—O—$(C_1-C_3)$alkyl, —$(CH_2)_2$—S—$CH_3$, benzyl and 4-hydroxybenzyl;
$R_6$ and $R_7$ are, independently, hydrogen or $(C_1-C_4)$alkyl; or taken together with the adjacent nitrogen atom form a 5-6 membered monocyclic saturated heterocycle, optionally containing one additional heteroatom chosen among —O— and —$NR_8$— where $R_8$ is hydrogen or $(C_1-C_3)$ alkyl;
with the proviso that when X is —S—, then Y is not OH or $O(C_1-C_4)$ alkyl
if the case, either as single optical isomers in the isolated form or mixture thereof in any proportion and their pharmaceutically acceptable salts.

More preferred compounds of formula (I) are the compounds wherein:
X is —O—, —S—;
Y is hydrogen or $O(C_1-C_3)$alkyl;
Z is =O or =S;
R is $(C_4-C_7)$alkyl or ω-trifluoro$(C_4-C_6)$alkyl;
$R_1$ and $R_2$ are, independently, hydrogen, $(C_1-C_3)$alkoxy, fluoro, chloro, trifluoromethyl or 2,2,2-trifluoroethyl; or one of $R_1$ and $R_2$ is in ortho position to R—X— and taken together with the same R—X—, represents a

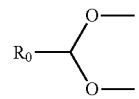

group where $R_0$ is $(C_3-C_4)$alkyl;
$R_3$ and $R'_3$ are, independently, hydrogen or $(C_1-C_3)$alkyl;

R$_4$ and R$_5$ are, independently, hydrogen or (C$_1$-C$_4$)alkyl; or R$_4$ is hydrogen and R$_5$ is a group selected from —CH$_2$—OH, —CH$_2$—O—(C$_1$-C$_3$)alkyl, benzyl and 4-hydroxybenzyl;

R$_6$ and R$_7$ are, independently, hydrogen or (C$_1$-C$_3$)alkyl; or taken together with the adjacent nitrogen atom form a 5-6 membered monocyclic saturated heterocycle, optionally containing one additional heteroatom chosen among —O— and —NR$_8$—, where R$_8$ is hydrogen or (C$_1$-C$_3$) alkyl;

with the proviso that when X is —S—, then Y is not O(C$_1$-C$_4$) alkyl;

if the case, either as single optical isomers in the isolated form or mixture thereof in any proportion and their pharmaceutically acceptable salts.

Even more preferred compounds of formula (I) are those compounds wherein:

X is —O—;
Y is hydrogen;
Z is =O;
R is (C$_4$-C$_6$)alkyl;
R$_1$ and R$_2$ are, independently, hydrogen or halo, preferably fluoro;
R$_3$, R'$_3$, R$_4$ and R$_5$ are hydrogen;
R$_6$ and R$_7$ are, independently, hydrogen or (C$_1$-C$_3$)alkyl;
if the case, either as single optical isomers in the isolated form or mixture thereof in any proportion and their pharmaceutically acceptable salts;

Most preferably, a compound of formula (I) according to this invention is selected from the group consisting of:
2-[2-(3-Butoxyphenyl)-ethylamino]-acetamide
2-[2-(3-Pentyloxyphenyl)-ethylamino]-acetamide
2-[2-(3-Hexyloxyphenyl)-ethylamino]-acetamide
2-[2-(3-Butoxyphenyl)-ethylamino]-N-methylacetamide
2-[2-(3-Pentyloxyphenyl)-ethylamino]-N-methylacetamide
2-[2-(3-Hexyloxyphenyl)-ethylamino]-N-methylacetamide
2-[2-(3-Butoxyphenyl)-ethylamino]-N,N-dimethylacetamide
2-[2-(3-Butylthiophenyl)-ethylamino]-N,N-dimethylacetamide
2-[2-(3-Butylsulfonylphenyl)-ethylamino]-N,N-dimethylacetamide
2-[2-(3-Butoxyphenyl)-(N'-hydroxy)ethylamino]-N,N-dimethylacetamide
2-[2-(3-Butoxyphenyl)-(N'-methoxy)ethylamino]-N,N-dimethylacetamide
2-[2-(3-Butoxyphenyl)-(N'-propoxy)ethylamino]-N,N-dimethylacetamide
2-[2-(3-Butoxyphenyl)-ethylamino]-N,N-dimethyl-thioacetamide
2-[2-(3-Butoxyphenyl)-2-methylpropylamino]-N,N-dimethylacetamide
2-{2-[3-(4,4,4-Trifluorobutoxy)phenyl]-ethylamino}-N,N-dimethylacetamide
2-[2-(3-Butylthiophenyl)-ethylamino]-N,N-dimethylacetamide
2-[2-(3-Butoxy-2-chlorophenyl)-ethylamino]-N,N-dimethylacetamide
2-[2-(3-Butoxy-2-fluorophenyl)-ethylamino]-N,N-dimethylacetamide
2-[2-(3-Butoxy-4-methoxyphenyl)-ethylamino]-N,N-dimethylacetamide
2-[2-(3-Butoxy-4-methylphenyl)-ethylamino]-N,N-dimethylacetamide
2-[2-(3-Butoxy-2,4-difluoro-4-methylphenyl)-ethylamino]-N,N-dimethylacetamide
2-[2-(3-Butoxy-2,6-difluoro-4-methylphenyl)-ethylamino]-N,N-dimethylacetamide
2-[2-(3-Butoxyphenyl)-ethylamino]-N,N-diethylacetamide
2-[2-(3-Butoxyphenyl)-ethylamino]-N,N-dipropylacetamide
2-[2-(3-Butoxyphenyl)-ethylamino]-N,N-dibutylacetamide
2-[2-(3-Pentyloxyphenyl)-ethylamino]-N,N-dimethylacetamide
2-[2-(3-Hexyloxyphenyl)-ethylamino]-N,N-dimethylacetamide
2-[2-(3-Butoxyphenyl)-ethylamino]-1-pyrrolidin-1-yl-ethan-1-one
2-[2-(3-Pentyloxyphenyl)-ethylamino]-1-pyrrolidin-1-yl-ethan-1-one
2-[2-(3-Hexyloxyphenyl)-ethylamino]-1-pyrrolidin-1-yl-ethan-1-one
2-[2-(3-Butoxyphenyl)-ethylamino]-N,N-dimethylpropanamide
2-[2-(3-Butoxyphenyl)-ethylamino]-3-hydroxy-N,N-dimethylpropanamide
2-[2-(3-Butoxyphenyl)-ethylamino]-3-methoxy-N,N-dimethylpropanamide
2-[2-(3-Butoxyphenyl)-ethylamino]-3-propoxy-N,N-dimethylpropanamide
2-[2-(3-Butoxyphenyl)-ethylamino]-2,N,N-trimethylpropanamide
2-[2-(3-Pentyloxyphenyl)-ethylamino]-2,N,N-trimethylpropanamide
2-[2-(3-Hexyloxyphenyl)-ethylamino]-2,N,N-trimethylpropanamide
(S)-2-[2-(3-Butoxyphenyl)-ethylamino]-propanamide
(S)-2-[2-(3-Butoxyphenyl)-ethylamino]-N-methylpropanamide
(S)-2-[2-(3-Butoxyphenyl)-ethylamino]-N,N-dimethylpropanamide
(R)-2-[2-(3-Butoxyphenyl)-ethylamino]-propanamide
(R)-2-[2-(3-Butoxyphenyl)-ethylamino]-N-methylpropanamide
(R)-2-[2-(3-Butoxyphenyl)-ethylamino]-N,N-dimethylpropanamide
2-[2-(3-Butoxy-2-trifluoromethylphenyl)-ethylamino]-N,N-dimethylacetamide
2-[2-(3-Butoxy-4-trifluoromethylphenyl)-ethylamino]-N,N-dimethylacetamide
2-[2-(3-Butoxy-5-trifluoromethylphenyl)-ethylamino]-N,N-dimethylacetamide if the case, either as single optical isomers in the isolated form or mixtures thereof in any proportion and their pharmaceutically acceptable salts, preferably their salts with hydrochloric or methanesulfonic acid.

The compounds of this invention are prepared according to conventional procedures which are described in more detail in the Experimental Part.

In particular most of the compounds of formula (I), where X is —O— and Y is hydrogen, object of the present invention, are prepared according to a synthetic process shown in the following Scheme I:

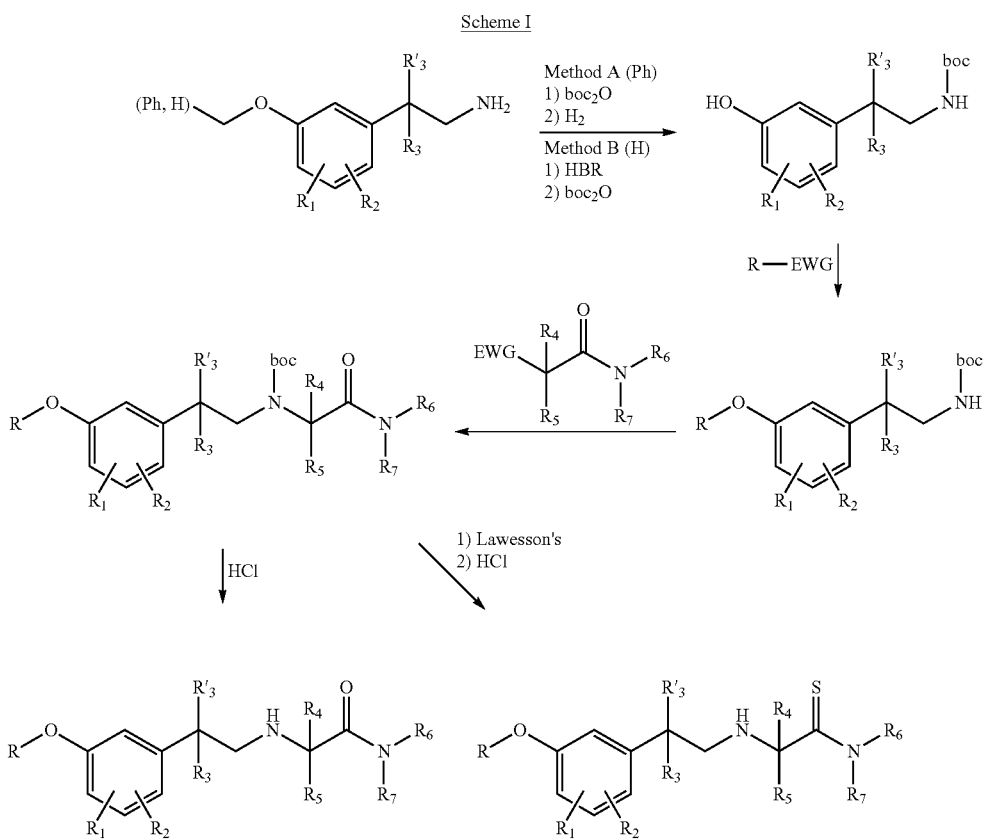

wherein:

R, $R_1$, $R_2$, $R_3$, $R'_3$, $R_4$, $R_5$, $R_6$ and $R_7$ have the same meanings defined in formula (I) above, Ph means a phenyl radical, boc is a tert-butoxycarbonyl group and EWG stays for "Electron Withdrawing Group" such as, for example, a halogen or a mesyloxy or a tosyloxy or a trifluoromethanesulfonate group. Lawessons's reagent is 2,4-bis(4-methoxyphenyl)-1,3,2,4-dithiadiphosphetane-2,4-disulfide (The Merck Index, 13$^{th}$ Ed., 5408, page 966).

According to a preferred embodiment of the invention the alkylation reactions with R-EWG are carried out in the presence of a base and, more preferably, said base is selected from $K_2CO_3$, triethylamine and diisopropylethylamine.

An alternative method for the preparation of the compounds of formula (I) where R, $R_1$, $R_2$, $R_3$, $R'_3$, $R_4$, $R_5$, $R_6$ and $R_7$ have the same meanings as in formula (I), X is O and Y is hydrogen consists in submitting an aldehyde of the formula

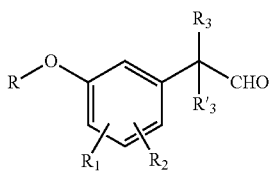

to a reductive alkylation with an α-aminoalkaneamide of formula

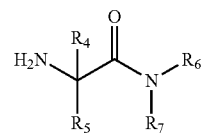

The reducing agent may be selected from $NaBH_4$, $NaBH_3CN$ and (polystyrylmethyl)-trimethylammonium cyanoborohydride.

The resulting 2-[2-(phenyl)ethylamino]alkaneamide compounds of formula (I) wherein Z is =O can be transformed into the corresponding compounds where Z is =S by protecting the —NH— group with $boc_2O$, reacting the N-boc protected derivative with Lawesson's reagent, and finally deprotecting with HCl as show in Scheme I.

As a further alternative to these methods, an amine of formula

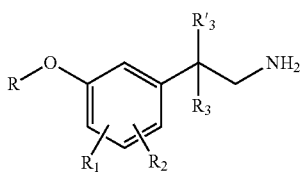

is alkylated by reaction with an ester of an alkanoic acid of formula

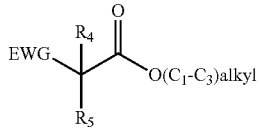

in the presence of a base (e.g. triethylamine) and the resulting alkanoic ester derivatives of formula

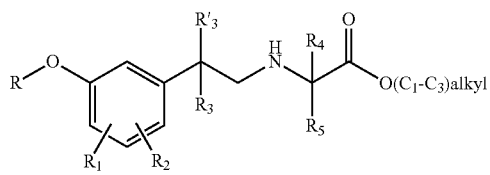

is reacted with an amine of formula $HNR_6R_7$, optionally in the presence of an amidation catalyst (e.g. trimethylaluminium), to yield the compound formula (I) where Y is hydrogen. The compounds of formula (I) where $R_5$ is hydrogen, optionally can be transformed into the corresponding compounds of formula (I) wherein $R_5$ is $(C_1\text{-}C_4)$alkyl, —$CH_2OH$, —$CH_2$—O—$(C_1\text{-}C_6)$ alkyl, —$CH(CH_3)$—OH, —$(CH_2)_2$—S—$CH_3$, benzyl, or 4-hydroxybenzyl by submitting a N-protected derivative of the above said compound of formula (I) to a C-alkylation procedure with an alkylating agent of formula $EWGR_5$ wherein EWG has the same meaning as above and $R_5$ represents one of the group listed hereinabove. In this case, when a end compound of formula (I) is desired where the group $R_5$ contain a hydroxy moiety, a reagent $EWGR_5$ is usually employed where the corresponding hydroxy moiety is protected, e.g. by acetylation. All protecting groups are then removed from the resulting C-alkylated compounds.

If desired, when a compound of formula (I) is obtained in a form of a free base it may be converted into a salt thereof (e.g., with hydrochloric acid) by common procedures.

The compounds of formula (I), where X is S or $SO_2$ and Y is hydrogen are prepared according to a synthetic process shown in the following Scheme II:

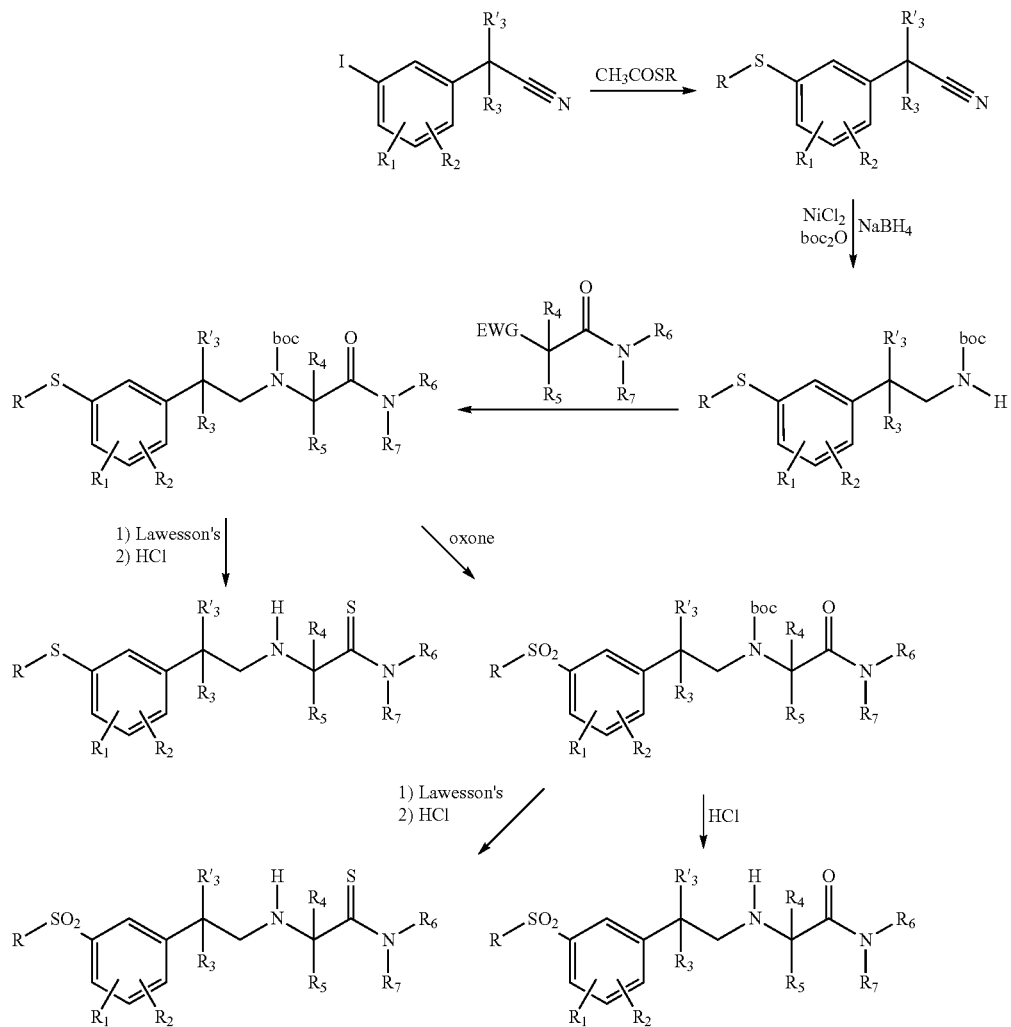

wherein

R, $R_1$, $R_2$, $R_3$, $R'_3$, $R_4$, $R_5$, $R_6$ and $R_7$ have the same meanings as defined in formula (I), boc is a tert-butoxycarbonyl group and EWG has the same meaning as above, "oxone" stays for potassium peroxymonosulfate and Lawessons's reagent is 2,4-bis(4-methoxyphenyl)-1,3,2,4-dithiadiphosphetane-2,4-disulfide.

The compounds of formula (I), where X is —O— and Y is OH or O($C_1$-$C_4$)alkyl, are prepared according to a synthetic process shown in the following Scheme III:

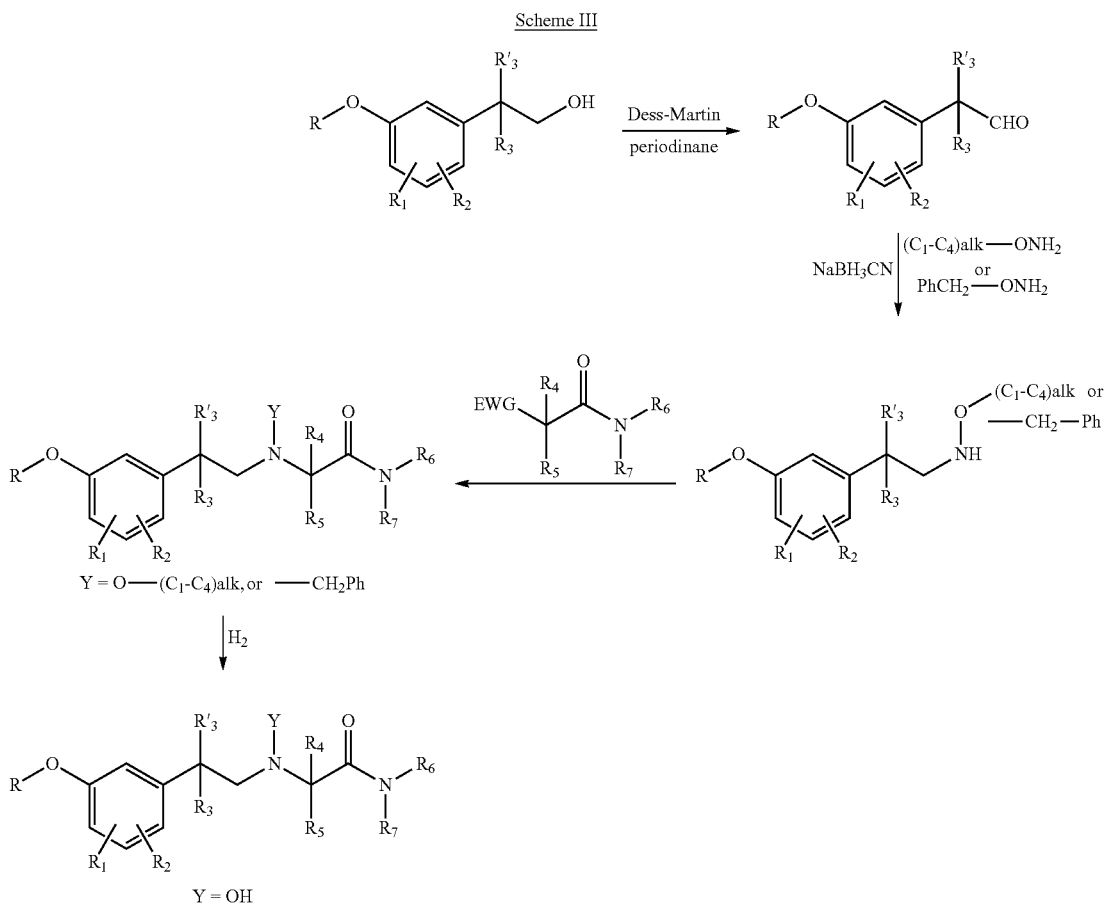

Scheme III wherein

R, $R_1$, $R_2$, $R_3$, $R'_3$, $R_4$, $R_5$, $R_6$ and $R_7$ have the same meanings as defined in formula (I), Ph means a phenyl group, and EWG has the same meaning as above. Dress-Martin periodinane, see: Dess, D. B.; Martin, J. C. J. Am. Chem. Soc., 1991, 113, 7277.

The intermediates used in Schemes I, II and III are commercially available or are prepared from commercially available compounds according to well-known methods.

The evaluation of the usefulness of the optional protection as well as the selection of the suitable protecting agent, according to the reaction carried out in the preparation of the compounds of the invention and the functional group to be protected, are within the common knowledge of the skilled person.

The removal of the optional protective groups is carried out according to conventional techniques.

For a general reference to the use of protective groups in organic chemistry see Theodora W. Greene and Peter G. M. Wuts "Protective groups in organic synthesis", John Wiley & Sons, Inc., II Ed., 1991.

The preparation of the salts of the compounds of formula (I) is carried out according to known methods.

For the preparation of a single optical isomer of a compound of formula (I) said compound may be obtained through a sterically controlled synthesis or by using reagents having the appropriate chirality or separating the desired isomer from the enantiomeric mixture thereof, according to conventional procedures.

Pharmacology

The compounds of the invention may be used for the manufacture of a medicament active as sodium and/or calcium channel modulator against disorders caused by dysfunctions of voltage gated sodium and/or calcium channels.

Such compounds are voltage-dependent blockers of the sodium and/or calcium channels with potency in the low micromolar range as demonstrated by the blockade of the sodium and/or calcium influx (fluorescence assays) and by the voltage-dependent blockade of the currents (patch clamp techniques).

The activity of the compounds representative of this invention was compared with that of compounds known from WO 90/14334, which have been clinically developed for therapeutical applications such as "ralfinamide" (S)-(+)-

2-[4-(2-fluorobenzyloxy)-benzylamino]-propanamide and/or "safinamide" (S)-(+)-2-[4-(3-fluorobenzyloxy)-benzylamino]-propanamide.

Safinamide (NW-1015, FCE-26743A, PNU-151774E) is a sodium channel blocker, a calcium channel modulator, a monoamino oxidase B (MAO-B) inhibitor, a glutamate release inhibitor and a dopamine metabolism modulator.

Safinamide is useful in the treatment of CNS disorders, in particular of epilepsy, Parkinson's disease, Alzheimer's disease, restless legs syndrome (WO 90/14334, WO 04/089353, WO 05/102300) and cognitive disorders (EP Appl. No 06/012352.8).

Ralfinamide (NW-1029, FCE-26742A, PNU-0154339E) is a sodium and calcium channel inhibitor and NMDA receptor modulator useful in the treatment of pain conditions, including neuropathic and inflammatory pain of both acute and chronic type, migraine, depressions, cardiovascular, inflammatory, urogenital, metabolic and gastrointestinal disorders (WO 99/35125, WO 03/020273, WO 04/062655, WO 05/018627, WO 05/070405, WO 06/027052).

The sodium channel modulating activity of the 2-[2-(phenyl)ethylamino]alkaneamide derivatives was measured through a fluorescence-based sodium influx assay in ND7/23 cell line (Table 1) and through the electrophysiological patch clamp technique in rat cortical neurons (Table 3) and in ND7/23 cell line (Table 4) respectively.

The calcium channel modulating activity of the 2-[2-(phenyl)ethylamino]alkaneamide derivatives was measured through a fluorescence-based calcium influx assays (Table 2) in AtT20 cell line.

The MAO-B activity of the above compounds was measured by using a radioenzymatic assay (Table 5) in rat brain mitochondria.

The in vivo analgesic activity of the above compounds was assessed in the "formalin test" in mice (Table 6) and in the "Spinal nerve ligation model of neuropathic pain (SNL)" in rats (FIG. 1). The anti-inflammatory pain activity was measured using the "Complete Freund's adjuvant model (CFA)" in rats.

Figure 2:
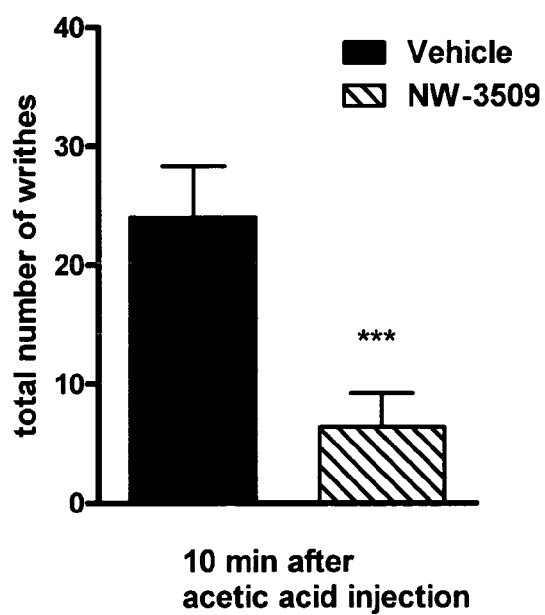
FIG. 2 provides results from testing of a mouse acetic acid-induced model of visceral pain, further described in Example 19.

The anti-visceral pain activity was measured using the "acetic acid-induced visceral pain" model in mice (FIG. 2).

The anticonvulsant activity was measured using the "Maximal electroshock test" in mice (Table 7 and Table 8).

The anti mania activity was measured using the "Amphetamine and chlordiazepoxide-induced hyperlocomotion in mice" model (FIG. 3) and in the "paradoxical sleep deprivation" rat model.

The antiamnesic activity was assessed using the "Morris Water Maze test" in which amnesia is induced by scopolamine in rats and in the "Novel Object Recognition test" in rats.

To investigate the antidepressant activity of the compounds the "Tail suspension test" model in mice was used.

Figure 4:
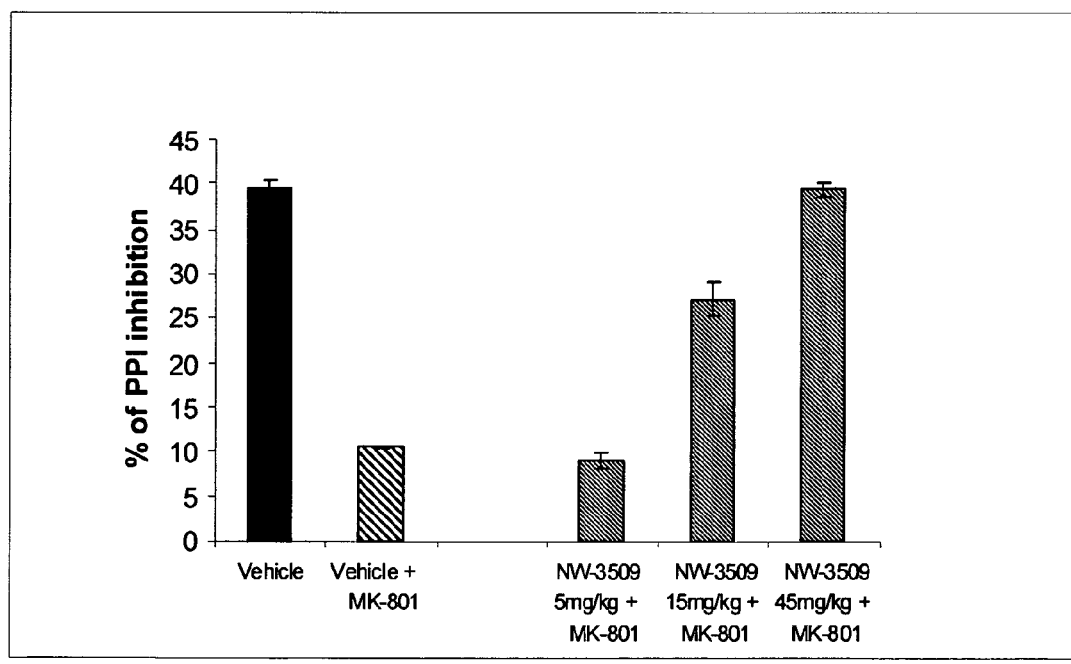
FIG. 4 provides results for a test of prepulse inhibition of startle (PPI) in mice and in rats, further described in Example 26.

The anti-schizophrenia activity was assessed using the "test of cognitive impairment in schizophrenia" and the "Prepulse inhibition of startle (PPI)" in mice and in rats (FIG. 4).

The "Cocaine-induced behavioural sensitization test" in rats was used to assess the anti-addiction activities of the compounds.

"Acute bladder irritation by acetic acid in rats" and "Intermediate bladder irritation by cyclophosphamide in rats" tests were used as models for urological diseases.

The anti migraine activity was measured using the "migraine test" in rats.

In electrophysiological patch clamp studies, such substances exhibit also "use and frequency-dependency", i.e. an enhancement of the block during a high frequency stimulation when there is a large accumulation of channels in the inactivated state, such as in neuronal pathological conditions. Functionally, the use-dependent block results in depression of neuronal activity at high frequency firing and with lower blocking capacity at normal firing rate suggesting that the compounds of this invention may selectively depress abnormal activity of the sodium and/or calcium channels, leaving unaffected the physiological activity, thus having limited CNS depressant effects (W. A. Catterall, Trends Pharmacol. Sci. (1987) 8: 57-65).

One of the most representative compounds of this invention is 2-[2-(3-Butoxyphenyl)-ethylamino]-N,N-dimethyl-acetamide hydrochloride (NW-3509) that was found very active in almost all experimental in vitro and in vivo models.

The compounds of the invention are active in vivo when orally, intraperitoneally or intravenously administered in the range of 0.1 to 100 mg/kg in different animal models here following described.

In view of the above described mechanisms of action, the compounds of the present invention are useful in the prevention or treatment of neuropathic pain. Neuropathic pain syndromes include, and are not limited to: diabetic neuropathy; sciatica; non-specific lower back pain; multiple sclerosis pain; fibromyalgia; HIV-related neuropathy; neuralgia, such as post-herpetic neuralgia and trigeminal neuralgia, Morton's neuralgia, causalgia; and pain resulting from physical trauma, amputation, phantom limb, cancer, toxins or chronic inflammatory conditions; central pain such as the one observed in thalamic syndromes, mixed central and peripheral forms of pain such as complex regional pain syndromes (CRPS) also called reflex sympathetic dystrophies.

The compounds of the invention are also useful for the treatment of chronic pain. Chronic pain includes, and is not limited to, chronic pain caused by inflammation or an inflammatory-related condition, osteoarthritis, rheumatoid arthritis, acute injury or trauma, upper back pain or lower back pain (resulting from systematic, regional or primary spine disease such as radiculopathy), bone pain (due to osteoarthritis, osteoporosis, bone metastasis or unknown reasons), pelvic pain, spinal cord injury-associated pain, cardiac chest pain, non-cardiac chest pain, central post-stroke pain, myofascial pain, sickle cell pain, cancer pain, Fabry's disease, AIDS pain, geriatric pain or pain caused by headache, temporomandibular joint syndrome, gout, fibrosis or thoracic outlet syndromes, in particular rheumatoid arthritis and osteoarthritis.

The compounds of the invention are also useful in the treatment of acute pain (caused by acute injury, illness, sports-medicine injuries, carpal tunnel syndrome, burns, musculoskeletal sprains and strains, musculotendinous strain, cervicobrachial pain syndromes, dyspepsis, gastric ulcer, duodenal ulcer, dysmenorrhoea, endometriosis or surgery (such as open heart or bypass surgery), post operative pain, kidney stone pain, gallbladder pain, gallstone pain, obstetric pain or dental pain.

The compounds of the invention are also useful in the treatment of headaches, migraine, tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

The compounds of the invention are also useful for the treatment of neurological conditions such as epilepsy including simple partial seizure, complex partial seizure, secondary generalized seizure, further including absence seizure, myoclonic seizure, clonic seizure, tonic seizure, tonic clonic seizure and atonic seizure. The compounds of the invention are also useful for the treatment of neurodegenerative disorders of various origins including Alzheimer Disease, Parkinson Disease and other dementia conditions such as Lewys body, fronto-temporal dementia and taupathies; amyotrophic lateral sclerosis and other parkinsonian syndromes; other spino cerebellar degeneration and Charcot-Marie-Toot neuropathy, traumatic brain injury, stroke and cerebral ischemia.

The compounds of the invention are also useful for the treatment of cognitive disorders and of psychiatric disorders. Examples of cognitive disorders are Mild Cognitive Impairment (MCI) and those associated to autism, dyslexia, attention deficit hyperactivity disorders, schizophrenia, obsessive compulsive disorders, psychosis, bipolar disorders, depression, Tourette's syndrome, and disorders of learning in children, adolescent and adults, Age Associated Memory Impairment, Age Associated Cognitive Decline, Alzheimer's Disease, Parkinson's Disease, Down's Syndrome, traumatic brain injury, Huntington's Disease, Progressive Supranuclear Palsy (PSP), HIV, stroke, vascular diseases, Pick's or Creutzfeldt-Jacob disease, multiple sclerosis (MS) and other white matter disorders and drug-induced cognitive worsening. Psychiatric disorders include, and are not limited to major depression, apathy, dysthymia, mania, bipolar disorder (such as bipolar disorder type I, bipolar disorder type II), cyclothymic disorder, rapid cycling, ultradian cycling, mania, hypomania, schizophrenia, schizophreniform disorders, schizoaffective disorders, personality disorders, attention disorders with or without hyperactive behaviour, delusional disorders, brief psychotic disorders, shared psychotic disorders, psychotic disorder due to a general medical condition, substance-induced psychotic disorders or a psychotic disorder not otherwise specified, anxiety disorders such as generalised anxiety disorder, panic disorders, post-traumatic stress disorder, impulse control disorders, phobic disorders, dissociative states and moreover in smoke and drug addiction and alcoholism. In particular bipolar disorders, schizophrenia, psychosis, anxiety and addiction.

The compounds of the invention inhibit inflammatory processes affecting all body systems. Therefore are useful in the treatment of inflammatory processes of the muscular-skeletal system of which the following is a list of examples but it is not comprehensive of all target disorders: arthritic conditions such as alkylosing spondylitis, cervical arthritis, fibromyalgia, gut, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: peri-arthritis nodosa, thyroiditis, aplastic anaemia, sclerodoma, myasthenia gravis, multiple sclerosis and other demyelinizating disorders, encephalomyelitis, sarcoidosis, nephritic syndrome, Bechet's syndrome, polymyositis, gingivitis.

Compounds of the invention are also useful in the treatment of gastrointestinal (GI) tract disorders such as inflammatory bowel disorders including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varialoforme, ulcerative colitis, peptic ulceration, pyresis, and other damage to the GI tract, for example, by *Helicobacter pylori*, gastroesophageal reflux disease, gastroparesis, such as diabetic gastroparesis; and other functional bowel disorders, such as non-ulcerative dyspepsia (NUD); emesis, diarrhoea, and visceral inflammation.

Compounds of the invention are also useful in the treatment of disorders of the genito-urinary tract such as overactive bladder, prostatitis (chronic bacterial and chronic non-bacterial prostatitis), prostadynia, interstitial cystitis, urinary incontinence and benign prostatic hyperplasia, annexities, pelvic inflammation, bartholinities and vaginitis. In particular overactive bladder and urinary incontinence.

It will be appreciated that the compounds of the invention may advantageously be used in conjunction with one or more other therapeutic agents. Examples of suitable agents for adjunctive therapy include a serotonin receptor modulator including a 5HT1B/1D agonist, such as a triptan (e.g. sumatriptan or naratriptan); an adenosine A1 agonist; an adenosine A2 antagonist; a purinergic P2X antagonist, an EP ligand; an NMDA modulator, such as a glycine antagonist; an AMPA modulator; a substance P antagonist (e.g. an NK1 antagonist); a cannabinoid; a nicotinic receptor agonist; an alpha-1 or 2 adrenergic agonist; acetaminophen or phenacetin; a 5-lipoxygenase inhibitor; a leukotriene receptor antagonist; a DMARD (e.g. methotrexate); gabapentin, pregabalin and related compounds; L-dopa and/or dopamine agonists; a catechol-O-methyltransferase inhibitor; a tricyclic antidepressant (e.g. amitryptiline); a neurone stabilising antiepileptic drugs; a monoaminergic uptake inhibitor (e.g. venlafaxine); a matrix metalloproteinase inhibitor; a nitric oxide synthase (NOS) inhibitor, such as an iNOS or an nNOS inhibitor; a free radical scavenger; an alpha-synuclein aggregation inhibitor; a cholinesterase inhibitor, a cholesterol lowering agent; an alpha-secretase modulator; a beta-secretase modulator; a beta-amyloid aggregation inhibitor; an inhibitor of the release, or action, of tumor necrosis factor alpha; an antibody therapy, such as monoclonal antibody therapy; an antiviral agent, such as a nucleoside inhibitor (e.g. lamivudine) or an immune system modulator (e.g. interferon); an opioid analgesic, such as morphine; a vanilloid receptor agonist and antagonist; an analgesic, such as a cyclooxygenase-1 and/or cyclooxygenase-2 inhibitor; a local anaesthetic such as lidocaine and derivatives; a stimulant, including caffeine; an H2-antagonist (e.g. ranitidine); a proton pump inhibitor (e.g. omeprazole); an antacid (e.g. aluminium or magnesium hydroxide; an antiflatulent (e.g. semethicone); a decongestant (e.g. phenylephrine, phenylpropanolamine, pseudoephedrine, oxymetazoline, epinephrine, naphazoline, xylometazoline, propylhexedrine, or levodesoxyephedrine, naphazoline, xylometazoline, propylhexedrine, or levo-desoxyephedrine); antitussive (e.g. codeine, hydrocodone, carmiphen, carbetapentane, or dextramethorphan); a diuretic; or a sedating or non-sedating antihistamine; an antipsychotic agent, including typical and atypical antipsychotics (e.g. haloperidol, risperidone, clozapine); an anti-depressant, such as a selective serotonin re-uptake inhibitors, serotonin and noradrenaline re-uptake inhibitors, MAO inhibitors and tryciclics antidepressant drugs; a mood stabilizer (e.g. lithium, lamotrigine, valproate); an anxiolytic agent (e.g. benzodiazepines, buspirone, beta-adrenergic receptors antagonists); morphine or morphine derivatives; other calcium or sodium channel blockers.

It is to be understood that the present invention covers the use of a compound of formula (I) or a pharmaceutically acceptable salt thereof in combination with one or more therapeutic agents.

The compounds of the present invention are useful in human and veterinary medicaments. It is to be understood that as used herein the terms "treatment" or "treating" whenever not specifically defined otherwise, include prevention, alleviation and cure of pathological afflictions, in particular, they include both the treatment of established symptoms and prophylactic treatment. Compounds of the present disclosure may preferably be used therapeutically and preventively as active ingredients in a pharmaceutical composition. Therefore, a further object of the present invention are pharmaceutical compositions containing a therapeutically effective amount of a compound of the invention or a salt thereof in admixture with a pharmaceutically acceptable carrier.

Accordingly, the expression "therapeutically effective" in the context of an "amount", a "dose" or "dosage" of the compounds of this invention is intended as an "amount", a "dose" or "dosage" of any said compounds sufficient for use in both the treatment of the established symptoms and the prophylactic treatment of the above said pathological afflictions.

The pharmaceutical compositions object of the present invention may be administered in a variety of immediate and modified release dosage forms, e.g. orally, in the form of tablets, troches, capsules, sugar or film coated tablets, liquid solutions, emulsions or suspensions; rectally, in the form of suppositories; parenterally, e.g. by intramuscular and/or depot formulations; intravenous injection or infusion; locally and transdermally in form of patch and gel and cream.

Suitable pharmaceutically acceptable, therapeutically inert organic and/or inorganic carrier materials useful in the preparation of such composition include, for example, water, gelatin, gum arabic, lactose, starch, cellulose, magnesium stearate, talc, vegetable oils, cyclodextrins, polyalkyleneglycols and the like.

The composition comprising the phenylethylamino derivatives of formula (I) as above defined can be sterilized and may contain further well known components, such as, for example, preservatives, stabilizers, wetting or emulsifying agents, e.g. paraffin oil, mannide monooleate, salts to adjust osmotic pressure, buffers and the like.

For example, the solid oral forms may contain, together with the active ingredient, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; desegregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The preparation of the pharmaceutical compositions object of the invention can be carried out according to common techniques.

The oral formulations comprise sustained release formulations that can be prepared in conventional manner, for instance by applying an enteric coating to tablets and granules.

The liquid dispersion for oral administration may be e.g. syrups, emulsions and suspensions. The syrups may contain as carrier, for example, saccharose or saccharose with glycerine and/or mannitol and/or sorbitol.

Suspensions and emulsions may contain as a carrier, for example, a natural gum, agar, sodium alginate, pectin, methylcellulose, carboxymethyl-cellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or preferably they may be in the form of sterile, aqueous, isotonic saline solutions.

The suppositories may contain, together with the active ingredient, a pharmaceutically acceptable carrier, e.g. cocoa butter, polyethylene glycol, a polyoxyethylene sorbitan fatty acid ester surfactants or lecithin.

The pharmaceutical compositions comprising the phenylethylamino derivatives of formula (I) as above defined will contain, per dosage unit, e.g., capsule, tablet, powder injection, teaspoonful, suppository and the like from about 0.1 to about 500 mg of one or more active ingredients most preferably from 1 to 10 mg.

Optimal therapeutically effective doses to be administered may be readily determined by those skilled in the art and will vary, basically, with the strength of the preparation, with the mode of administration and with the advancement of the condition or disorder treated. In addition, factors associated with the particular subject being treated, including subject age, weight, diet and time of administration, will result in the need to adjust the dose to an appropriate therapeutically effective level.

It is to be understood that while the invention is described in conjunction of the preferred embodiments thereof, those skilled in the art are aware that other embodiment could be made without departing from the spirit of the invention.

EXPERIMENTAL PART

The $^1$H-NMR spectra have been determined in solution of $CDCl_3$ or DMSO-$d_6$ with a Varian Gemini 200 MHz spectrometer. The chemical shifts are defined as δ with $CDCl_3$ or DMSO-$d_6$ and $D_2O$ as inner standard.

The HPLC/MS analyses are determined with a Gilson instrument by utilizing a X-Terra RP18 column (5 μm, 4.6×50 mm) coupled to a UV detector (220 nm) and a Finnigan Aqa mass spectrometer (electron spray, positive ionization mode). Conditions utilized for the analyses: flow: 1.2 ml/min; column temperature: 50° C.; A/B elution gradient (eluent A: 0.1% formic acid in water; eluent B: 0.1% formic acid in acetonitrile): 5-95% of B from 0 to 8.0 minutes, 95% of B from 8.0 to 9.5 minutes.

For better illustrating the invention the following examples are now given.

Example 1

2-[2-(3-Butoxyphenyl)-ethylamino]-N,N-dimethylacetamide hydrochloride

The compound was synthesized according to Scheme I

Step 1: 2-(3-Hydroxyphenyl)-(tert-butoxycarbonyl)ethylamine

Method A

To a suspension of 2-(3-benzyloxyphenyl)-ethylamine hydrochloride (12.6 g, 47.7 mmol) in $H_2O$ (120 ml) and 1M NaOH (95 ml), a solution of $boc_2O$ (15.6 g, 71.5 mmol) in THF (120 ml) was added dropwise and the mixture was stirred at room temperature. After 16 h the organic solvent was removed under reduced pressure and the mixture was extracted with $CH_2Cl_2$ (2×100 ml). The collected organic phases were dried over $Na_2SO_4$, the solution was filtered and the solvent evaporated under reduced pressure to give a crude oil that was used without further purification.

$^1$H NMR (300 MHz, $CDCl_3$): δ 7.47-7.28 (m, 5H), 7.22 (m, 1H), 6.87-6.77 (m, 3H), 5.05 (s, 2H), 4.52 (bs, 1H), 3.38 (dt, J=6.5 Hz, J=6.5 Hz, 2H), 2.77 (t, J=7.1 Hz, 2H), 1.44 (s, 9H).

ESI$^+$MS: calcd for $C_{20}H_{25}NO_3$: 327.43. found: 328.1 (MH$^+$).

The 2-(3-Benzyloxyphenyl)-(tert-butoxycarbonyl)ethylamine obtained in Step 1 and 10% Pd/C (1.3 g) in MeOH (240 ml), was hydrogenated in a Parr apparatus for 16 h at 35 psi. The catalyst was removed by filtration on Celite pad and the solvent was evaporated under reduced pressure. The crude oil was used without further purification.

$^1$H NMR (300 MHz, $CDCl_3$): δ 7.19 (dd, J=7.8 Hz, J=7.8 Hz, 1H), 6.82-6.66 (m, 3H), 4.56 (bs, 1H), 3.39 (dt, J=7.0 Hz, J=6.3 Hz, 2H), 2.76 (t, J=7.0 Hz, 2H), 1.46 (s, 9H).

ESI$^+$MS: calcd for $C_{13}H_{19}NO_3$: 237.30. found: 238.2 (MH$^+$).

Method B

A 33% solution of HBr in acetic acid (150 ml) was cooled to 0° C. and 3-methoxy phenethylamine (10.0 g, 66.0 mmol) was added portionwise. The mixture was heated to 80° C. and stirred for 16 h. The solvent was evaporated under reduced pressure and the residue was dissolved in water (160 ml). 4 M NaOH (15 ml) was added followed by 2 M of NaOH (130 ml). A solution of $boc_2O$ (15.8 g, 72.6 mmol) in THF (160 ml) was added dropwise and the mixture was stirred at room temperature for 16 h. The upper organic layer of the resulting mixture was separated and the aqueous layer was extracted with $CH_2Cl_2$ (3×100 ml). The combined organic solutions were dried over $Na_2SO_4$, filtered and the solvent was evaporated under reduced pressure. The crude title compound (16.8 g) was obtained as a brown gum that was used in the following steps without further purification.

ESI$^+$MS: calcd for $C_{13}H_{19}NO_3$: 237.3. found: 182.1 (MH$^+$-t-butyl, major fragment).

Step 2: 2-(3-Butoxyphenyl)-(tert-butoxycarbonyl)ethylamine

To a solution in acetone (240 ml), of 2-(3-hydroxyphenyl)-(tert-butoxycarbonyl)ethylamine obtained in Step 1, $K_2CO_3$ (19.8 g) and 1-bromobutane (15 ml) were added. The suspension was refluxed for 3 days and the solvent was evaporated under reduced pressure. The residue was dissolved in $H_2O$ (200 ml) and extracted with $CH_2Cl_2$ (2×200 ml). The solvent was eliminated under reduced pressure and the residue was purified by flash chromatography (petroleum ether/EtOAc 85:15) affording 1 (11.3 g, 81% over 3 steps) of the title compound as colorless oil.

$^1$H NMR (300 MHz, $CDCl_3$): δ 7.22 (dd, J=7.6 Hz, J=7.6 Hz, 1H), 6.81-6.72 (m, 3H), 4.55 (bs, 1H), 3.97 (t, J=6.3 Hz, 2H), 3.39 (dt, J=6.5 Hz, J=6.5 Hz, 2H), 2.78 (t, J=7.1 Hz, 2H), 1.78 (m, 2H), 1.51 (m, 2H), 1.45 (s, 9H), 0.99 (t, J=7.3 Hz, 3H).

ESI$^+$MS: calcd for $C_{17}H_{27}NO_3$: 293.41. found: 294.1 (MH$^+$).

Step 3: 2-[2-(3-Butoxyphenyl)-(tert-butoxycarbonyl)ethylamino]-N,N-dimethylacetamide To a suspension of NaH (60%, 2.0 g, 51 mmol) in dry DMF (125 ml) cooled at 0° C., a solution of 2-(3-butoxyphenyl)-(tert-butoxycarbonyl)ethylamine (7.5 g, 25.5 mmol) in dry DMF (125 ml) was added dropwise. After 1 h at room temperature, 2-chloro-N,N-dimethylacetamide (5.2 ml, 51 mmol) was added and the mixture was stirred for 16 h at room temperature. $H_2O$ (10 ml) was added and the solvent was evaporated under reduced pressure. The residue was dissolved in $H_2O$ (150 ml) and extracted with $CH_2Cl_2$ (2×150 ml). The collected organic phases were dried over $Na_2SO_4$, filtered and evaporated. The crude was purified by flash chromatography (petroleum ether/EtOAc 4:6) affording the title compound (7.2 g, 75%) as light yellow oil.

$^1$H NMR (300 MHz, DMSO-d6): δ 7.1 (m, 1H), 6.79-6.71 (m, 3H), 3.97 (t, J=6.0 Hz, 2H), 3.96 (s, 2H), 3.40 (dd, J=8.7 Hz, J=7.2 Hz, 2H), 2.88 (s, 6H), 2.76 (dd, J=7.9 Hz, J=6.4 Hz, 2H), 1.76 (m, 2H), 1.46 (m, 2H), 1.37 (s, 9H), 0.95 (t, J=7.3 Hz, 3H).

ESI$^+$MS: calcd for $C_{21}H_{34}N_2O_4$: 378.52. found: 379.0 (MH$^+$).

Step 4: 2-[2-(3-Butoxyphenyl)-ethylamino]-N,N-dimethylacetamide hydrochloride

A solution of 2-[2-(3-butoxyphenyl)-(tert-butoxycarbonyl)ethylamino]-N,N-dimethylacetamide (9.6 g, 25.3 mmol) in HCl/$Et_2O$ (127 ml) was stirred at room temperature for 16 h. The solvent was evaporated under reduced pressure, the residue was ground with a mixture of $Et_2O$/$iPr_2O$ 50/50, filtered and washed with $Et_2O$/$iPr_2O$ to obtain the title compound as white solid (1.71 g, yield 95%).

$^1$H NMR (300 MHz, $CDCl_3$): δ 9.63 (br. s., 1H), 7.23 (dd, 1H), 6.83-6.91 (m, 2H), 6.80 (ddd, 1H), 3.96 (s, 2H), 3.96 (t, 2H), 3.32-3.44 (m, 2H), 3.22-3.32 (m, 2H), 2.97 (s, 6H), 1.70-1.83 (m, 2H), 1.41-1.58 (m, 2H), 0.99 (t, 3H).

ESI$^+$MS: calcd for $C_{16}H_{26}N_2O_2$: 278.40. found: 279.3 (MH$^+$).

Analogously, starting from the appropriate intermediates, the following compounds were prepared:

2-[2-[3-(4,4,4-Trifluorobutoxy)phenyl]-ethylamino]-N,N-dimethylacetamide hydrochloride $^1$H NMR (300 MHz, DMSO-d6): δ 9.00 (br. s., 2H), 7.17-7.32 (m, 1H), 6.78-6.94 (m, 3H), 4.04 (br. s., 2H), 3.91-4.20 (m, 2H), 3.08-3.22 (m, 2H), 2.93-3.00 (m, 2H), 2.94 (s, 3H), 2.90 (s, 3H), 2.30-2.48 (m, 2H), 1.78-2.05 (m, 2H).

ESI⁺MS: calcd for $C_{16}H_{23}F_3N_2O_2$ (free base): 332.27. found: 333.25 (MH⁺).

2-[2-(3-Pentyloxyphenyl)-ethylamino]-N,N-dimethylacetamide hydrochloride

¹H NMR (300 MHz, DMSO-d6): δ 9.03 (br s, 2H), 7.14-7.29 (m, 1H), 6.70-6.88 (m, 3H), 4.03 (s, 2H), 3.95 (t, 2H), 3.06-3.21 (m, 2H), 2.94 (s, 3H), 2.90 (s, 3H), 2.81-3.02 (m, 2H), 1.62-1.80 (m, 2H), 1.23-1.48 (m, 4H), 0.90 (t, 3H).
ESI⁺MS: calcd for $C_{17}H_{28}N_2O_2$ (free base): 292.42. found: 293.25 (MH⁺).

2-[2-(3-Hexyloxyphenyl)-ethylamino]-N,N-dimethylacetamide hydrochloride

¹H NMR (300 MHz, DMSO-d6): δ 9.01 (br s, 2H), 7.23 (dd, 1H), 6.65-6.93 (m, 3H), 4.03 (s, 2H), 3.95 (t, 2H), 3.05-3.24 (m, 2H), 2.94 (s, 3H), 2.91-3.01 (m, 2H), 2.90 (s, 3H), 1.57-1.84 (m, 2H), 1.35-1.51 (m, 2H), 1.22-1.36 (m, 4H), 0.70-1.01 (m, 3H).
ESI⁺MS: calcd for $C_{18}H_{30}N_2O_2$ (free base): 306.45. found: 307.32 (MH⁺).

2-[2-(3-Butoxyphenyl)-ethylamino]-N,N-dipropylacetamide hydrochloride

¹H NMR (300 MHz, DMSO-d6): δ 8.88 (br. s., 2H), 7.15-7.30 (m, 1H), 6.68-6.88 (m, 3H), 4.02 (s, 2H), 3.96 (t, 2H), 3.23-3.28 (m, 2H), 3.09-3.22 (m, 4H), 2.87-2.98 (m, 2H), 1.62-1.75 (m, 2H), 1.35-1.62 (m, 6H), 0.94 (t, 3H), 0.85 (dt, 6H).
ESI⁺MS: calcd for $C_{20}H_{34}N_2O_2$ (free base): 334.50. found: 335.34 (MH⁺).

2-[2-(3-Butoxyphenyl)-ethylamino]-N,N-dibutylacetamide hydrochloride

¹H NMR (300 MHz, DMSO-d6+TFA): δ 8.85 (br. s., 2H), 7.19-7.28 (m, 1H), 6.62-6.88 (m, 3H), 4.01 (t, 2H), 3.96 (t, 2H), 3.30 (t, 2H), 3.06-3.24 (m, 4H), 2.85-3.00 (m, 2H), 1.61-1.82 (m, 2H), 1.40-1.55 (m, 6H), 1.20-1.38 (m, 4H), 0.94 (t, 6H), 0.89 (t, 3H).
ESI⁺MS: calcd for $C_{20}H_{38}N_2O_2$ (free base): 362.55. found: 363.35 (MH⁺).

2-[2-(3-Pentyloxyphenyl)-ethylamino]-N,N-dipropylacetamide hydrochloride

¹H NMR (300 MHz, DMSO-d6+Na₂CO₃): δ 7.50 (br. s., 1H) 7.07-7.24 (m, 1H) 6.62-6.83 (m, 3H) 3.93 (t, 2H) 3.06-3.22 (m, 5H) 2.58-2.81 (m, 5H) 1.62-1.78 (m, 2H) 1.28-1.56 (m, 8H) 0.68-0.99 (m, 9H).
ESI⁺MS: calcd for $C_{21}H_{36}N_2O_2$ (free base): 348.53. found: 349.28 (MH⁺).

2-[2-(3-Butoxyphenyl)-ethylamino]-acetamide hydrochloride

¹H NMR (300 MHz, DMSO-d6): δ 8.96 (br s, 2H), 7.87 (br s, 1H), 7.54 (br s, 1H), 7.23 (dd, 1H), 6.58-6.83 (m, 3H), 3.96 (t, 2H), 3.70 (s, 2H), 3.04-3.18 (m, 2H), 2.82-3.01 (m, 2H), 1.57-1.80 (m, 2H), 1.32-1.54 (m, 2H), 0.81-1.04 (m, 3H).
ESI⁺MS: calcd for $C_{14}H_{22}N_2O_2$: 250.34. found: 251.1 (MH⁺).

2-[2-(3-Butoxyphenyl)-ethylamino]-N-methylacetamide hydrochloride

¹H NMR (300 MHz, DMSO-d6): δ 8.99 (br s, 2H), 8.39 (q, 1H), 7.08-7.37 (m, 1H), 6.65-6.95 (m, 3H), 3.96 (t, 2H), 3.70 (s, 2H), 3.04-3.25 (m, 2H), 2.79-3.04 (m, 2H), 2.67 (d, 3H), 1.57-1.82 (m, 2H), 1.44 (sxt, 2H), 0.94 (t, 3H).
ESI⁺MS: calcd for $C_{15}H_{24}N_2O_2$: 264.37. found: 265.2 (MH⁺).

2-[2-(3-Isopropoxyphenyl)-ethylamino]-N,N-dimethylacetamide hydrochloride

¹H NMR (300 MHz, DMSO-d6): δ 9.04 (br s, 2H), 7.12-7.32 (m, 1H), 6.70-6.81 (m, 3H), 4.60 (spt, 1H), 4.03 (s, 2H), 3.04-3.21 (m, 2H), 2.94 (s, 3H), 2.91-3.01 (m, 2H), 2.90 (s, 3H), 1.26 (d, 6H).
ESI⁺MS: calcd for $C_{15}H_{24}N_2O_2$: 264.37. found: 265.2 (MH⁺).

2-[2-(3-Butoxyphenyl)-ethylamino]-N,N-diethylacetamide hydrochloride

¹H NMR (300 MHz, DMSO-d6): δ 8.89-8.98 (br s, 2H), 7.24 (dd, 1H), 6.72-6.88 (m, 3H), 4.03 (s, 2H), 3.96 (t, 2H), 3.34 (q, 2H), 3.26 (q, 2H), 3.08-3.21 (m, 2H), 2.86-3.03 (m, 2H), 1.59-1.78 (m, 2H), 1.33-1.54 (m, 2H), 1.13 (t, 3H), 1.07 (t, 3H), 0.94 (t, 3H).
ESI⁺MS: calcd for $C_{18}H_{30}N_2O_2$: 306.45. found: 307.2 (MH⁺).

2-[2-(3-Butoxyphenyl)-ethylamino]-1-pyrrolidin-1-yl-ethanone

¹H NMR (300 MHz, DMSO-d6): δ 8.94 (s, 2H), 7.14-7.33 (m, 1H), 6.64-6.93 (m, 3H), 4.00 (t, 2H), 3.88 (s, 2H), 3.33-3.45 (m, 4H), 3.19-3.29 (m, 2H), 2.96-3.05 (m, 2H), 1.78-2.00 (m, 4H), 1.65-1.78 (m, 2H), 1.37-1.56 (m, 2H), 0.96 (t, 3H).
ESI⁺MS: calcd for $C_{18}H_{28}N_2O_2$: 304.44. found: 305.2 (MH⁺).

2-[2-(3-Butoxy-4-fluorophenyl)-ethylamino]-N,N-dimethylacetamide hydrochloride ¹H NMR (300 MHz, DMSO-d6): δ 8.91 (br s, 2H) 7.15 (dd, 1H) 7.05 (dd, 1H) 6.79 (ddd, 1H) 3.97-4.12 (m, 4H) 3.09-3.21 (m, 2H) 2.94 (s, 3H) 2.92-2.99 (m, 2H) 2.90 (s, 3H) 1.65-1.82 (m, 2H) 1.36-1.54 (m, 2H) 0.87-1.01 (m, 3H).
ESI⁺MS: calcd for $C_{16}H_{25}N_2O_2$ (free base): 296.38. found: 297.22 (MH⁺).

2-[2-(3-Butoxy-4-methoxyphenyl)-ethylamino]-N,N-dimethylacetamide hydrochloride ¹H NMR (300 MHz, DMSO-d6): δ 8.97 (br s, 2H), 6.90 (d, 1H), 6.84 (d, 1H), 6.74 (dd, 1H), 4.02 (br s, 2H), 3.94 (t, 2H), 3.73 (s, 3H), 3.04-3.22 (m, 2H), 2.94 (s, 3H), 2.90 (s, 3H), 2.84-2.92 (m, 2H), 1.57-1.84 (m, 2H), 1.44 (sxt, 2H), 0.94 (t, 3H).
ESI⁺MS: calcd for $C_{17}H_{28}N_2O_3$ (free base): 308.42. found: 309.21 (MH⁺).

Example 2

2-[2-(3-Butoxyphenyl)-ethylamino]-2,N,N-trimethylpropanamide hydrochloride

Step 1: 2-[2-(3-Butoxyphenyl)-ethylamino]-2-methylpropionic acid ethyl ester To a solution of 2-(3-butoxyphenyl)- ethylamine hydrochloride (0.27 g, 1.42 mmol; obtained from the compound of Step 2 of Example 1, according to the standard procedure described in Step 4 of Example 1) in acetonitrile (8 ml), 2-bromo-2-methylpropionic acid ethyl ester (0.27 ml, 1.85 mmol) and triethylamine (0.52 ml, 3.70 mmol) were added. The solution was heated at 100° C. under microwave irradiation for 3 h. The mixture was cooled to room temperature and partitioned between water and $CH_2Cl_2$. The organic layer was separated, washed with brine, dried over $Na_2SO_4$, filtered and the solvent was evaporated under reduced pressure. The residue was purified by flash chromatography (silica, $CH_2Cl_2$:MeOH from 100:0 to 95:5) affording the title compound (0.17 g, 39% yield) as colourless oil.

ESI$^+$MS: calcd for $C_{18}H_{29}NO_3$: 307.44. found: 308.2 (MH$^+$).

Step 2: 2-[2-(3-Butoxyphenyl)-ethylamino]-2,N,N-trimethylpropanamide hydrochloride To a solution of dimethylamine, 2 M in THF (0.6 ml, 1.1 mmol) in toluene (3 ml) trimethylaluminium, 2 M in hexane (1.4 ml, 2.77 mmol) was added and the mixture was stirred at room temperature for 15 minutes. 2-[2-(3-butoxyphenyl)-ethylamino]-2-methylpropionic acid ethyl ester (0.17 g, 0.55 mmol) in dry toluene (8 ml) was added and the solution was heated to 90° C. and stirred for 24 h. The mixture was cooled to room temperature and the solved removed under reduced pressure. The residue was partitioned between water and diethyl ether. The organic layer was separated, washed with brine, dried over $Na_2SO_4$, filtered and the solvent was evaporated under reduced pressure. The residue was purified by flash chromatography (first purification: silica, $CH_2Cl_2$:MeOH from 100:0 to 97:3; second purification: silica, EtOAc) affording the title compound that was dissolved in HCl/Et$_2$O and stirred for 20 minutes. The resulting hydrochloride salt was filtered, washed with iPr$_2$O and dried at 40° C. under vacuum. The pure title compound (18.5 mg, 20% yield) was obtained as a white solid.

$^1$H NMR (300 MHz, CDCl$_3$): δ 9.39 (bs, 2H), 7.24 (t, 1H), 6.71-6.97 (m, 3H), 3.97 (t, 2H), 3.13-3.36 (m, 4H), 3.09 (s, 6H), 1.90 (s, 6H), 1.69-1.86 (m, 2H), 1.51 (sxt, 2H), 0.99 (t, 3H).

ESI$^+$MS: calcd for $C_{18}H_{30}N_2O_2$: 306.45. found: 307.32 (MH$^+$).

Example 3

2-[2-(3-Butoxyphenyl)-ethylamino]-N,N-dimethyl-propanamide hydrochloride

Step 1: 2-[2-(3-Butoxyphenyl)-(tert-butoxycarbonyl)ethylamino]-N,N-dimethylpropanamide A solution of 2-[2-(3-butoxyphenyl)-(tert-butoxycarbonyl)ethylamino]-N,N-dimethylacetamide (0.410 g, 1.1 mmol; prepared according to Step 3 of Example 1) in dry THF (5 ml) was cooled to −78° C. and LiHMDS (lithium hexamethyldisilazide), 1 M in THF, (1.43 ml, 1.4 mmol) was added dropwise. The mixture was stirred 30 min then a solution of methyl iodide (0.187 g, 1.3 mmol) in dry THF (1 ml) was added dropwise. The mixture was stirred for 2 h allowing the cooling bath to expire. The solvent was evaporated under reduced pressure and the residue was dissolved in EtOAc (15 ml) and washed with water (2×15 ml). The organic phase was dried over $Na_2SO_4$, filtered and the solvent was evaporated under reduced pressure. The residue was purified by flash chromatography (silica, petroleum ether:EtOAc from 8:2 to 6:4) affording the title compound (0.22 g, 52% yield) as a colourless oil.

ESI$^+$MS: calcd for $C_{22}H_{36}N_2O_4$: 392.54. found: 393.3 (MH$^+$).

Step 2: 2-[2-(3-Butoxyphenyl)-ethylamino]-N,N-dimethylpropanamide hydrochloride The title compound was prepared from 2-[2-(3-butoxyphenyl)-(tert-butoxycarbonyl)ethylamino]-N,N-dimethylpropanamide according to the standard procedure described in Step 4 of Example 1. White solid (47% yield).

$^1$H NMR (300 MHz, DMSO-d6): δ 9.16 (br s, 1H), 8.82 (br s, 1H), 7.14-7.31 (m, 1H), 6.64-6.93 (m, 3H), 4.39 (q, 1H), 3.96 (t, 2H), 3.08-3.22 (m, 1H), 3.00 (s, 3H), 2.96-3.06 (m, 1H), 2.87-2.96 (m, 2H), 2.90 (s, 3H), 1.59-1.82 (m, 2H), 1.37-1.53 (m, 2H), 1.38 (d, 3H), 0.94 (t, 3H).

ESI$^+$MS: calcd for $C_{17}H_{28}N_2O_2$ (free base): 292.42. found: 293.25 (MH$^+$).

Example 4

2-[2-(3-Butoxyphenyl)-ethylamino]-3-hydroxy-N,N-dimethylpropanamide hydrochloride

Step 1: 2-[2-(3-Butoxyphenyl)-(tert-butoxycarbonyl)ethylamino]-3-acetoxy-N,N-dimethyl-propanamide The title compound was prepared from [2-[2-(3-butoxyphenyl)-(tert-butoxycarbonyl)ethylamino]-N,N-dimethylacetamide and acetic acid bromomethyl ester according to Step 1 of Example 3. Colourless oil (38% yield).

ESI$^+$MS: calcd for $C_{24}H_{38}N_2O_6$ (free base): 450.58. found: 451.2 (MH$^+$).

Step 2: 2-[2-(3-Butoxyphenyl)-(tert-butoxycarbonyl)ethylamino]-3-hydroxy-N,N-dimethyl-propanamide 2-[2-(3-Butoxyphenyl)-(tert-butoxycarbonyl)ethylamino]-3-acetoxy-N,N-dimethylpropanamide (0.19 g, 0.42 mmol) was dissolved in 3% NH$_4$OH/MeOH (15 ml) and stirred at room temperature for 5 h. The solvent was evaporated under reduced pressure and the residue was purified by flash chromatography (silica, petroleum ether:EtOAc from 7:3 to 3:7) affording the title compound (0.13 g, 66% yield) as a colourless oil.

ESI$^+$MS: calcd for $C_{22}H_{36}N_2O_5$: 408.54. found: 409.2 (MH$^+$).

Step 3: 2-[2-(3-Butoxyphenyl)-ethylamino]-3-hydroxy-N,N-dimethylpropanamide hydrochloride The title compound was prepared from 2-[2-(3-butoxyphenyl)-(tert-butoxycarbonyl)ethylamino]-3-acetoxy-N,N-dimethylpropanamide according to the standard procedure described in Step 4 of Example 1. Obtained as white solid (76% yield).

$^1$H NMR (300 MHz, DMSO-d6): δ 8.46-9.44 (m, 2H) 7.10-7.33 (m, 1H) 6.65-6.92 (m, 3H) 5.54 (t, 1H) 4.44 (t, 1H) 3.95 (t, 2H) 3.65-3.88 (m, 2H) 3.11-3.22 (m, 1H) 3.03-3.09 (m, 1H) 3.02 (s, 3H) 2.91-2.99 (m, 2H) 2.90 (s, 3H) 1.61-1.79 (m, 2H) 1.35-1.53 (m, 2H) 0.86-1.00 (m, 3H).

ESI$^+$MS: calcd for $C_{17}H_{28}N_2O_3$ (free base): 308.42. found: 309.21 (MH$^+$).

Example 5

2-[2-(3-Butoxy-4-methylphenyl)-ethylamino]-N,N-dimethylacetamide hydrochloride

Step 1: (3-Hydroxy-4-methylphenyl)-acetonitrile

To a solution of 3-methoxy-4-methylphenylacetonitrile (2.0 g, 12.4 mmol) in dry $CH_2Cl_2$ (50 ml) cooled to −78° C., $BBr_3$ 1 M in $CH_2Cl_2$ (27 ml, 27 mmol) was added dropwise. The mixture was stirred overnight allowing the cooling bath to expire. The mixture was slowly poured in ice/water under stirring. When the ice melted, the aqueous phase was extracted with EtOAc and the organic phase was dried over $Na_2SO_4$, filtered and the solvent was evaporated under reduced pressure. The crude title compound (1.7 g, 93% yield) was used in the next step without further purification.

Step 2: (3-Butoxy-4-methylphenyl)-acetonitrile

To a solution of (3-hydroxy-4-methylphenyl)-acetonitrile (1.7 g, 11.5 mmol) in acetone (100 ml), $K_2CO_3$ (7.9 g, 57.5 mmol) and 1-bromo butane (6.1 ml, 57.5 mmol) were added. The suspension was refluxed for 24 h and the solvent was evaporated under reduced pressure. The residue was dissolved in $CH_2Cl_2$ and washed with water and brine. The organic layer was dried over $Na_2SO_4$, filtered and the solvent evaporated under reduced pressure. The crude was purified by flash chromatography (petroleum ether:EtOAc 9.5:0.5) affording the title compound (1.43 g, 61% yield) as colourless oil.

ESI$^+$MS: calcd for $C_{13}H_{17}NO$: 203.29. found: 204.1 (MH$^+$).

Step 3: N-[2-(3-Butoxy-4-methylphenyl)-ethyl]-carbamic acid tert-butyl ester To a solution of (3-butoxy-4-methylphenyl)acetonitrile (0.94 g, 5.0 mmol) in methanol (38 ml), nickel chloride hexahydrate (0.12 g, 0.5 mmol) and boc$_2$O (2.18 g, 10.0 mmol) were added. The solution was cooled to 0° C. and sodium borohydride (1.32 g, 35.0 mmol) was added portionwise over 30 minutes. The mixture was stirred overnight allowing the cooling bath to expire. The reaction was quenched by addition of diethylenetriamine (0.54 ml, 5 mmol) and stirred for 30 minutes. The solvent was removed under reduced pressure and the residue re-dissolved in EtOAc, washed with water, dried over $Na_2SO_4$, filtered and the solvent was evaporated under reduced pressure. The crude was purified by flash chromatography (silica, petroleum ether:EtOAc 90:10) to give the title compound. Colourless oil (80% yield).

ESI$^+$MS: calcd for $C_{18}H_{29}NO_3$: 307.44. found: 308.1 (MH$^+$).

Step 4: 2-[2-(3-Butoxy-4-methylphenyl)-ethylamino]-N,N-dimethylacetamide hydrochloride The title compound was prepared from [2-(3-butoxy-4-methylphenyl)-ethyl]-carbamic acid tert-butyl ester according to the standard procedures described in Steps 3 and 4 of Example 1. Obtained as white solid.

$^1$H NMR (300 MHz, DMSO-d6): δ 8.93 (br s, 2H), 7.08 (dd, 1H), 6.79 (d, 1H), 6.69 (dd, 1H), 4.03 (s, 2H), 3.97 (t, 2H), 3.08-3.19 (m, 2H), 2.93 (s, 3H), 2.91-2.97 (m, 2H), 2.90 (s, 3H), 2.11 (s, 3H), 1.65-1.79 (m, 2H), 1.39-1.54 (m, 2H), 0.95 (t, 3H).

ESI$^+$MS: calcd for $C_{17}H_{28}N_2O_2$ (free base): 292.42. found: 293.25 (MH$^+$).

Analogously, starting from (2,6-difluoro-3-methoxyphenyl)-acetonitrile the following compound was prepared:

2-[2-(3-Butoxy-2,6-difluorophenyl)-ethylamino]-N,N-dimethylacetamide hydrochloride $^1$H NMR (300 MHz, DMSO-d6): δ 9.16 (br s, 2H), 7.07-7.18 (m, 1H), 6.96-7.07 (m, 1H), 4.07 (s, 2H), 4.02 (t, 2H), 3.08 (s, 4H), 2.93 (s, 3H), 2.90 (s, 3H), 1.63-1.76 (m, 2H), 1.36-1.51 (m, 2H), 0.93 (t, 3H).

ESI$^+$MS: calcd for $C_{16}H_{24}F_2N_2O_2$ (free base): 314.37. found: 315.20 (MH$^+$).

Example 6

2-[2-(3-Butoxyphenyl)-2-methylpropylamino]-N,N-dimethylacetamide hydrochloride

Step 1: 2-(3-Methoxyphenyl)-2-methylpropionitrile

To a solution of (3-methoxyphenyl)-acetonitrile (8.0 g, 0.054 mol) in DMF (25 ml) cooled to 0° C., NaH (1.3 g, 0.054 mol) was added. The reaction was stirred for 30 min, and MeI (3.3 mL, 0.054 mol) was added. The reaction was stirred 1 h at room temperature. After this period, the reaction mixture was cooled again to 0° C., NaH (1.3 g, 0.054 mol) was added followed by MeI (3.3 ml, 0.054 mol) after 30 minutes. The reaction was stirred at room temperature overnight. DMF was evaporated and the crude diluted with brine and extracted with Et$_2$O. The organic phase was washed with water, dried over $Na_2SO_4$, the solvent was evaporated under reduced pressure and the residue was purified by flash chromatography (petroleum ether:AcOEt 95:5) to give the title compound (4 g, 42% yield) as a colourless oil.

ESI$^+$MS: calcd for $C_{11}H_{13}NO$: 175.23. found: 176.1 (MH$^+$).

Step 2: 2-[2-(3-Butoxyphenyl)-2-methylpropylamino]-N,N-dimethylacetamide hydrochloride The title compound was prepared from 2-(3-methoxyphenyl)-2-methylpropionitrile according to the procedure described in Example 5.

$^1$H NMR (300 MHz, DMSO-d6): δ 8.44 (br. s., 2H), 7.28 (t, 1H), 6.90-7.04 (m, 2H), 6.77-6.90 (m, 1H), 3.99 (t, 2H), 3.88 (s, 2H), 3.16 (s, 2H), 2.88 (s, 6H), 1.64-1.78 (m, 2H), 1.42-1.55 (m, 2H), 1.36-1.42 (m, 6H), 0.90-1.04 (m, 3H).

ESI$^+$MS: calcd for $C_{18}H_{30}N_2O_2$ (free base): 306.45. found: 307.26 (MH$^+$).

Example 7

2-[2-(3-Butylthiophenyl)-ethylamino]-N,N-dimethylacetamide hydrochloride

Step 1: (3-Butylthiophenyl)-acetonitrile

To a solution of (3-iodophenyl)-acetonitrile (2.0 g, 8.2 mmol) and acetic acid S-butyl ester (2.4 ml, 24.6 mmol) in n-BuOH (5 ml), CuI (0.156 g, 0.8 mmol), ethylene glycol (0.96 ml, 1.7 mmol) and $K_2CO_3$ (2.4 g, 17.3 mmol) were added and the mixture was heated under microwave irradiation to 110° C. for 1 h. The reaction mixture was diluted with AcOEt and filtered over a celite pad. The organic phase was washed with water and brine, dried over $Na_2SO_4$ and the solvent was evaporated under reduced pressure. The crude was purified by flash chromatography (petroleum ether:AcOEt from 10:0 to 9:1) to give pure title compound as a pale yellow oil (1.0 g, 64% yield), used without further purification in the next step.

ESI$^+$MS: calcd for $C_{12}H_{15}NS$: 205.32, no mass detectable.

Step 2: 2-[2-(3-Butylthiophenyl)-ethylamino]-N,N-dimethylacetamide hydrochloride The title compound was prepared from (3-butylthiophenyl)-acetonitrile according to the procedure described in Example 5.

$^1$H NMR (300 MHz, DMSO-d6): δ 9.08 (br. s., 2H), 7.23-7.36 (m, 1H), 7.15-7.23 (m, 2H), 6.95-7.11 (m, 1H), 4.03 (s, 2H), 3.08-3.21 (m, 2H), 2.92-3.02 (m, 4H), 2.94 (s, 3H), 2.90 (s, 3H), 1.49-1.67 (m, 2H), 1.30-1.49 (m, 2H), 0.89 (t, 3H).

ESI$^+$MS: calcd for $C_{16}H_{26}N_2OS$ (free base): 294.46. found: 295.20 (MH$^+$).

Example 8

2-[2-(3-Butylsulfonylphenyl)-ethylamino]-N,N-dimethylacetamide hydrochloride

Step 1: 2-[2-(3-Butylsulfonylphenyl)-(tert-butoxycarbonyl)ethylamino]-N,N-dimethylacetamide To a solution of 2-[2-(3-butylthiophenyl)-(tert-butoxycarbonyl)ethylamino]-N,N-dimethylacetamide hydrochloride (0.25 g, 0.62 mmol; prepared from the compound of Step 2 of Example 7, by reaction with boc$_2$O according to the procedure described in the first part of Step 1 of Example 1) in acetonitrile (20 ml)/water (10 ml), a mixture of oxone (0.92 g, 1.5 mmol) and NaHCO$_3$ (0.2 g, 2.3 mmol) was added portionwise over 5 minutes. The mixture was stirred at room temperature for 2 h. The mixture was partitioned between water and CH$_2$Cl$_2$, the organic was washed with water and brine, dried over Na$_2$SO$_4$ and the solvent was evaporated under reduced pressure. The crude was purified by flash chromatography (petroleum ether:AcOEt 3:7) to give pure title compound as a colourless oil (0.20 g, 75% yield).

ESI$^+$MS: calcd for $C_{21}H_{34}N_2O_5S$: 426.58. found: 427.1 (MH$^+$).

Step 2: 2-[2-(3-Butylsulfonylphenyl)-ethylamino]-N,N-dimethylacetamide hydrochloride The title compound was prepared from 2-[2-(3-butylsulfonylphenyl)-(tert-butoxycarbonyl)ethylamino]-N,N-dimethylacetamide according to the standard procedure described in Step 4 of Example 1.

$^1$H NMR (300 MHz, DMSO-d6+TFA): δ 8.84-9.10 (m, 2H), 7.74-7.86 (m, 2H), 7.57-7.71 (m, 2H), 4.06 (t, 2H), 3.03-3.34 (m, 6H), 2.95 (s, 3H), 2.91 (s, 3H), 1.45-1.63 (m, 2H), 1.24-1.42 (m, 2H), 0.84 (s, 3H).

ESI$^+$MS: calcd for $C_{16}H_{26}N_2OS$ (free base): 294.46. found: 295.20 (MH$^+$).

Example 9

2-[2-(3-Butoxyphenyl)-ethylamino]-N,N-dimethylthioacetamide hydrochloride

Step 1: 2-[2-(3-Butoxyphenyl)-(tert-butoxycarbonyl)ethylamino]-N,N-dimethylthioacetamide To a solution of 2-[2-(3-butoxyphenyl)-(tert-butoxycarbonyl)ethylamino]-N,N-dimethylacetamide (0.38 g, 1.0 mmol) in dry toluene (20 ml), Lawesson's reagent (0.58 g, 1.2 mmol) was added one-pot and the mixture was heated to reflux and stirred for 2 h. The solvent was evaporated under reduced pressure and the residue was purified by flash chromatography (petroleum ether:AcOEt from 9:1 to 8:2) to give pure title compound as a colourless oil (0.11 g, 28% yield).

ESI$^+$MS: calcd for $C_{21}H_{34}N_2O_3S$: 394.58. found: 395.1 (MH$^+$).

Step 2: 2-[2-(3-Butoxyphenyl)-ethylamino]-N,N-dimethylthioacetamide hydrochloride The title compound was prepared from 2-[2-(3-butoxyphenyl)-(tert-butoxycarbonyl)ethylamino]-N,N-dimethylthioacetamide according to the standard procedure described in Step 4 of Example 1. Obtained as white solid.

$^1$H NMR (300 MHz, DMSO-d6): δ 8.88 (s, 2H), 7.16-7.34 (m, 1H), 6.73-6.88 (m, 3H), 4.17 (s, 2H), 3.96 (dd, 2H), 3.43 (s, 3H), 3.31 (s, 3H), 3.16-3.26 (m, 2H), 2.92-3.04 (m, 2H), 1.62-1.76 (m, 2H), 1.36-1.50 (m, 2H), 0.94 (t, 3H).

ESI$^+$MS: calcd for $C_{16}H_{26}N_2OS$ (free base): 294.46. found: 295.22 (MH$^+$).

Example 10

2-[2-(3-Butoxyphenyl)]-(N'-methoxy)ethylamino]-N,N-dimethylacetamide

Step 1: 2-(3-Butoxyphenyl)-acetaldehyde

To a solution of 2-(3-butoxyphenyl)-ethanol (3.00 g, 15.4 mmol; prepared from 2-(3-hydroxyphenyl)-ethanol according to the procedure described in Step 2 of Example 1) in CH$_2$Cl$_2$ (100 ml), Dess-Martin periodinane reagent (8.5 g, 20.1 mmol) was added and the reaction was left at room temperature overnight. The solution was poured into a NaHCO$_3$ saturated solution containing Na$_2$S$_2$O$_3$ (35 g), and the mixture was stirred for 30 min. The organic layer was separated, dried over Na$_2$SO$_4$, filtered and evaporated under reduced pressure.

The residue containing the title compound (2.9 g, 99% yield) was used in the next step without further purification.

Step 2: 2-(3-Butoxyphenyl)-(N-methoxy)ethylamine

To a suspension of 2-(3-butoxypheny)-acetaldehyde (2.00 g, 10.4 mmol) and 0-methoxyamine hydrochloride (1.12 g, 13.4 mmol) in water (13 ml), a solution of Na$_2$CO$_3$ (0.66 g, 6.2 mmol) in water (20 ml) was added dropwise under stirring at 0° C. The reaction was left at room temperature overnight and then extracted with diethylether. The organic layer was dried over Na$_2$SO$_4$, filtered and evaporated under reduced pressure.

The residue containing the desired oxime intermediate (2.24 g, 10.2 mmol) was dissolved in methanol (60 ml) and acetic acid (8.8 ml, 153.0 mmol) was added. The solution was cooled to 0° C. and NaCNBH$_3$ was added portionwise. The reaction mixture was stirred at room temperature overnight, then the solvent was removed under reduced pressure and the residue was partitioned between 5% NaHCO$_3$ solution and ethyl acetate. The organic phase was dried over Na$_2$SO$_4$, filtered and concentrated to dryness under vacuum. The crude residue was purified by column chromatography, (petroleum ether:ethyl acetate 9:1) to afford 0.88 g (38% yield) of the title compound.

Step 3: 2-[2-(3-Butoxyphenyl)]-(N'-methoxy)ethylamino]-N,N-dimethylacetamide 2-(3-Butoxyphenyl)-(N-methoxy)ethylamine (0.5 g, 2.25 mmol), obtained as described in Step 2, was dissolved in acetonitrile (15 ml) and ethyldiisopropylamine (1.95 ml, 11.25 mmol) was added followed by 2-chloro-N,N-dimethylacetamide (1.15 ml, 11.25 mmol). The solution was heated at 130° C. under microwave irradiation for 6 h. The mixture was cooled to room temperature, the solvent removed under reduced pressure and the residue was partitioned between 5% NaHCO$_3$ and ethyl acetate. The organic phase was dried over Na$_2$SO$_4$, filtered and concentrated to dryness under vacuum. The crude residue was purified by column chromatography, (petroleum ether:ethyl acetate 1:1) to afford 0.25 g (36% yield) of the title compound.

$^1$H NMR (300 MHz, DMSO-d6+TFA): 7.17 (t, 1H), 6.61-6.89 (m, 3H), 3.94 (t, 2H), 3.56 (s, 2H), 3.47 (s, 3H), 2.98 (s, 3H), 2.89-2.97 (m, 2H), 2.80 (s, 3H), 2.72-2.86 (m, 2H), 1.58-1.77 (m, 2H), 1.34-1.53 (m, 2H), 0.93 (t, 3H).

ESI$^+$MS: calcd for C$_{17}$H$_{28}$N$_2$O$_3$ (free base): 308.42. found: 309.18 (MH$^+$).

Example 11

TTXs-Sodium Channel Influx Assay

ND7/23 rat dorsal root ganglion-derived cell line endogenously expresses a mixed population of TTXs sodium channels. These cells lack of TTXr sodium channels as shown by the absence of their respective transcripts.

ND7/23 cells were grown in DMEM supplemented with 10% FBS and 1 mM sodium piruvate. The cells were seeded at 50,000 cells/well on 96 poly-L-lysine-coated plates and further incubated for 18-24 h before use.

The Membrane Potential Kit Assay (Molecular Devices), based on a negatively charged fluorescent dye able to monitor changes in membrane potential caused by the sodium influx due to the channel opening, was used for the assay.

Cells were incubated with the dye loading for 30 minutes at 25° C. Then, 100 nM of the toxin *Anemonia sulcata* (used as enhancer of the channel opener response) alone or in the presence of TTX (as reference standard) or test compound were added for further 15 minutes.

The fluorescence (excitation: 530 nm, emission: 565 nm wavelength) was measured before and after (40-45 s) the automated injection of the sodium channel opener veratridine (100 μM) using a Victor plate reader (Perkin Elmer).

The inhibition curves were calculated from 5 concentrations, each in triplicate, and the IC$_{50}$ determined using linear regression analysis.

The compounds of the present invention inhibit TTXs sodium channels with pharmacologically significant IC$_{50}$ values.

The results, obtained with some compounds which are representative of the entire class of compounds of the invention, compared with the standards ralfinamide and safinamide, are reported in Table 1.

TABLE 1

| Compound | Na$^+$ influx IC$_{50}$ μM |
|---|---|
| 2-[2-(3-Hexyloxyphenyl)-ethylamino]-N,N-dimethylacetamide hydrochloride | 0.5 |
| 2-[2-(3-Butoxyphenyl)-ethylamino]-N,N-dipropylacetamide hydrochloride | 0.5 |
| 2-[2-(3-Pentyloxyphenyl)-ethylamino]-N,N-dimethylacetamide hydrochloride | 0.5 |
| 2-[2-(3-Butoxyphenyl)-ethylamino]-N,N-diethylacetamide hydrochloride | 0.6 |
| 2-[2-(3-Butoxyphenyl)-ethylamino]-2,N,N-trimethylpropanamide hydrochloride | 0.7 |
| 2-[2-(3-Butoxy-4-methylphenyl)-ethylamino]-N,N-dimethylacetamide hydrochloride | 0.7 |
| 2-[2-(3-Pentyloxyphenyl)-ethylamino]-N,N-dipropylacetamide hydrochloride | 1.1 |
| 2-[2-(3-Butoxyphenyl)-ethylamino]-N,N-dimethylpropanamide hydrochloride | 1.1 |
| 2-[2-(3-Butoxyphenyl)-ethylamino]-N,N-dibutylacetamide hydrochloride | 1.2 |
| 2-[2-(3-Butoxyphenyl)-ethylamino]-N,N-dimethylthioacetamide hydrochloride | 1.2 |
| 2-[2-(3-Butoxyphenyl)-ethylamino]-N,N-dimethylacetamide hydrochloride | 1.5 |
| 2-[2-(3-Butoxyphenyl)-ethylamino]-1-pyrrolidin-1-yl-ethanone hydrochloride | 2.1 |
| 2-[2-(3-Butoxy-2,6-difluorophenyl)-ethylamino]-N,N-dimethylacetamide hydrochloride | 2.6 |
| (S)-(+)-2-[4-(2-Fluorobenzyloxy)-benzylamino]-propanamide (ralfinamide)* | 9.5 |
| (S)-(+)-2-[4-(3-Fluorobenzyloxy)-benzylamino]-propanamide (safinamide)* | 7.4 |

*as the salt with methanesulfonic acid

Example 12

Calcium Channel Influx Assay

AtT20/D16v-F2 mouse pituitary tumour cell line preferentially expresses L-type calcium channels.

AtT20 cells were grown in DMEM with 10% of FBS, 4 mM glutamine. The cells were seeded at 200,000 cells/well on 96 poly-L-lysine-coated plates and further incubated for 18-24 h, before use.

The Ca$^{++}$ Kit Assay (Molecular Devices), which is based on a fluorescent calcium indicator to detect the calcium influx determined by depolarizing conditions, was used for the assay.

Cells were incubated with the calcium dye loading for 30 min at 37° C. Then, ω-conotoxin alone (1 μM) or in presence of nifedipine (as reference standard) or test compound were added for further 15 min.

The fluorescence (excitation: 485-emission: 535 nm wavelength) was measured before and after (30-40 sec) the automated injection of 100 mM KCl depolarizing solution using a Victor plate reader (Perkin Elmer).

The inhibition curves were calculated from 5 concentrations, each in triplicate, and the IC$_{50}$ determined using linear regression analysis.

The results, obtained with some compounds which are representative of the entire class of compounds of the invention, compared with the standards ralfinamide and safinamide, are reported in Table 2.

TABLE 2

| Compound | $Ca^{++}$ influx $IC_{50}$ μM |
|---|---|
| 2-[2-(3-Butoxyphenyl)-ethylamino]-N,N-dipropylacetamide hydrochloride | 1.1 |
| 2-[2-(3-Butoxyphenyl)-ethylamino]-N,N-dibutylacetamide hydrochloride | 1.8 |
| 2-[2-(3-Hexyloxyphenyl)-ethylamino]-N,N-dimethylacetamide hydrochloride | 4.0 |
| 2-[2-(3-Butoxyphenyl)-ethylamino]-N,N-diethylacetamide hydrochloride | 6.7 |
| 2-[2-(3-Pentyloxyphenyl)-ethylamino]-N,N-dipropylacetamide hydrochloride | 6.9 |
| 2-[2-(3-Butylthiophenyl)-ethylamino]-N,N-dimethylacetamide hydrochloride | 7.2 |
| 2-[2-(3-Butoxyphenyl)-ethylamino]-N,N-dimethylthioacetamide hydrochloride | 7.6 |
| 2-[2-(3-Pentyloxyphenyl)-ethylamino]-N,N-dimethylacetamide hydrochloride | 8.3 |
| 2-{2-[3-(4,4,4-Trifluorobutoxy)phenyl]-ethylamino}-N,N-dimethylacetamide hydrochloride | 9.3 |
| 2-[2-(3-Butoxy-4-methylphenyl)-ethylamino]-N,N-dimethylacetamide hydrochloride | 10.0 |
| (S)-(+)-2-[4-(2-Fluorobenzyloxy)-benzylamino]-propanamide (ralfinamide)* | 26.0 |
| (S)-(+)-2-[4-(3-Fluorobenzyloxy)-benzylamino]-propanamide (safinamide)* | 33.0 |

*as the salt with methanesulfonic acid

Example 13

Patch Clamp Evaluation of Na⁺ Currents Blockade in Rat Cortical Neurons

Cell Preparation and Culturing

Procedures involving animals and their care were conducted in conformity with institutional guidelines in compliance with national (D.L. n.116, G.U., suppl.40, Feb. 18, 1992) and international laws and policies (EEC Council directive 86/609, OJL358.1, Dec. 12, 1987; Guide for the Care and Use of Laboratory Animals, U.S. National Research Council, 1996). Cortical neurons were prepared from embryonic Wistar rats (E17-E19). A female rat at date 17-19 of pregnancy was anesthetized and sacrificed. The fetuses (n=4-5) were dissected and placed in ice-cold Hank's solution (Hank's solution (Life tech.14170-088)+glucose 30%+Pen-Strep 100× (Life Tech. 15140-122) 100 U-100 μg/ml and Hepes-NaOH 5 mM). The uterus and placenta were removed, the fetuses were decapitated and the heads were placed in ice-cold Hank's solution.

The skin of the head was removed using a pincer, the scalp was opened cutting laterally from the back till the eyes, and the brain was taken out using a curved pincer.

The brain was cut in two halves, the outer connective tissue membrane was removed with a pincer, and, keeping the brain upside down, the cerebellum, the brainstem and the diencephalon was removed using a curved pincer trying to clean as much as possible the inside of the cortex.

Each cortex was cut in smaller parts with a scissors, the pieces were transferred to a 15 ml centrifuge tube using a 5 ml pipette and washed twice with Hank's solution.

The solution was removed except 1-2 ml and the tissue was first dissociated with a 5 ml pipette then with two fire-polished Pasteur pipettes (medium and small opening, respectively). After the mechanical dissociation, 5 ml of complete DMEM (Dulbecco's modified Eagle medium) (Gibco 41966-029)+FBS (Hyclone) 10%+Glutamine (Life Tech. 25030-024) 2 mM+Pen-Strep 100 U-100 μg/ml were added, and cell suspension was centrifuged for 5 min at 1000 rpm. Supernatant was removed and 5 ml of complete Neurobasal medium was added (NB medium (Life tech.21103-049)+B27 (Life tech.17504-044) 2%+Glutamine 2 mM+Pen-Strep 100 U-100 μg/ml).

Cells were counted and diluted in Neurobasal medium to a concentration of 400000 cells per poly-D-lysine 5 μg/ml treated Petri dish.

Cortical neurons were used from day $6^{th}$ till day $11^{th}$ after plating, and once a week Neurobasal medium was changed.

Whole Cell Patch Clamp Recordings

Experiments on cortical neurons were carried out using standard whole cell patch clamp methods (Hamill et al., Pfugers Arch., 1981 August 391(12), 85-100). Membrane currents were recorded and filtered at 5 kHz with an Axon Axopatch 200B amplifier and data digitized with an Axon Digidata 1322A (Axon Instruments, CA, USA). Protocol playing and data acquisition were controlled online with Axon pClamp8 software. Measuring and reference electrodes were AgCl—Ag electrodes. A Sutter Instrument P-87 Puller (CA, USA) was used for pulling patch clamp pipettes with a resistance of 2-3 MΩ from Harward borosilicate glass tubes. Cells were continuously superfused with extracellular solutions, using a solution changer Biologic RSC-200.

Voltage Protocols and Data Analyses

To test the effect of compounds on sodium currents in cortical neurons, cells were clamped at −90 mV, then a two step protocol was used to determine the voltage dependence of the block. Sodium currents were activated by a 30 ms step pulse to −10 mV (test pulse) from a 2000 ms preconditioning potential of −110 mV (resting condition) and a potential of ∼−50 mV (half maximal steady-state condition).

Tonic block of resting and depolarized currents at a given drug concentration, was calculated as the difference between the peak Na⁺ current in the control external bath solution and peak currents with the test substance divided by control peak.

Drug concentration-inhibition curves were obtained by plotting tonic blocks in the resting and depolarized condition, versus drug concentrations. Dose-response curves were fitted to the tonic block data, according to the logistic equation: $y=A2+(A1−A2)/[1+(x/IC_{50})p]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor.

The apparent affinity of drug for the inactivated state (Ki) was calculated according to the equation $1/Kdep=h/Kr+(1-h)/Ki$ where Kr is the affinity of drug for the resting/closed state; Kdep is the $IC_{50}$ in the depolarized condition, h and (1-h) are the fractions of channels present at the rest and dep potentials, respectively.

Solutions and Drugs

Control bath solution contained (mM): NaCl 60, CholineCl 60, CaCl2 1.3, MgCl2 2, KCl 2, CdCl2 0.4, NiCl2 0.3, TEACl 20, Hepes 10, Glucose 10.

Internal pipette solution consisted of (mM): CsF 65, CsCl 65, NaCl 10, CaCl2 1.3, MgCl2 2, Hepes 10, EGTA 10, MgATP 1.

Compounds were dissolved as stock solutions (20 mM) in DMSO. They were diluted to the final concentrations in the external solution.

Results

The compounds of this invention are able to block Na⁺ currents in rat cortical neurons. The results obtained with 2-[2-(3-butoxyphenyl)-ethylamino]-N,N-dimethylacetamide hydrochloride (NW-3509), a representative compound of the chemical class of this invention, compared with our standards safinamide and ralfinamide, are reported in Table 3.

TABLE 3

| COMPOUND | $IC_{50}$ resting (Kr) (μM) | $IC_{50}$ depolarized (μM) | Ki |
|---|---|---|---|
| 2-[2-(3-Butoxyphenyl)-ethylamino]-N,N-dimethylacetamide hydrochloride | 25 | 0.8 | 0.4 |
| (S)-(+)-2-[4-(3-Fluorobenzyloxy)-benzylamino]-propanamide (safinamide)* | >100 (180) | 7.0 | 3.6 |
| (S)-(+)-2-[4-(2-Fluorobenzyloxy)-benzylamino]-propanamide (ralfinamide)* | >100 (213) | 9.0 | 4.7 |

*as the salt with methanesulfonic acid

Data expressed as $IC_{50}$ value at μM concentration, as well as the affinity for the inactivated state (Ki) demonstrate that the compound of this invention is a very potent and voltage dependent sodium channel blocker.

Example 14

Patch Clamp Evaluation of $Na^+$ Currents Blockade in ND7/23 Cell Line

Cell Line Maintenance

ND7/23 (ECACC No 92090903 from SIGMA) is a hybrid cell line derived from a neonatal rat DRG fused with the mouse neuroblastoma N18Tg2 (Wood et al., Proc. Biol. Sci., 1990 September, 241 (1302), 187-194). ND7/23 cells exhibit sensory neuron-like properties and express tetrodotoxin-sensitive (TTX-s) but not tetrodotoxin-resistant (TTX-r) currents (Zhou et al., J. Pharmacol. Exp. Ther., 2003 August, 306(2), 498-504; John et al., Neuropharmacology, 2004 March 46(3), 425-438)). The lack of TTX-r currents is consistent with the absence of TTX-r channel transcripts in these cells.

The molecular identity of the channels responsible for the TTX-s conductance is unknown but it is presumed that TTX-s conductance arises from the activity of a mixed population of sodium channels.

Cells are routinously maintained in DMEM with 10% of FBS, 4 mM glutamine, 1 mM sodium piruvate. The day before the patch clamp experiment cells are detached and seeded at 100,000 cells/polylysine-coated 35 mm Petri dish.

Whole Cell Patch Clamp Recordings

Experiments on ND7/23 cells were carried out using standard whole cell patch clamp methods (Hamill et al., Pfughers Arch., 1981 August 391(12), 85-100), as described in previous section.

Voltage Protocols and Data Analyses

To test the effect of compounds on sodium currents in ND7/23 cells, holding membrane potential was set at −90 mV, then a two step protocol was used to determine the voltage dependence of the block. Sodium currents were activated by a 30 ms step pulse to 0 mV (test pulse) from a 2000 ms preconditioning potential of −110 mV (resting condition) and a potential of ∼−70 mV (half maximal steady-state condition).

Tonic block of resting and depolarized currents at a given drug concentration was calculated as the difference between the peak $Na^+$ current in the control external bath solution and peak currents with the test substance divided by control peak.

Drug concentration-inhibition curves were obtained by plotting tonic blocks in the resting and depolarized condition, versus drug concentrations. Dose-response curves were fitted to the tonic block data, according to the logistic equation: $y=A2+(A1-A2)[1+(x/IC_{50})p]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor.

The apparent affinity of drug for the inactivated state (Ki) was calculated according to the equation $1/Kdep=h/Kr+(1-h)/Ki$ where Kr is the affinity of drug for the resting/closed state; Kdep is the $IC_{50}$ in the depolarized condition, h and (1-h) are the fractions of channels present at the rest. and dep. potentials, respectively.

Solutions and Drugs

Control bath solution contained (mM): NaCl 80, Choline HCl 40, CaCl2 1.3, MgCl2 2, KCl 2, CdCl2 0.4, NiCl2 0.3, TEACl 20, Hepes 10, Glucose 10.

Internal pipette solution consisted of (mM): CsF 65, CsCl 65, NaCl 10, CaCl2 1.3, MgCl2 2, Hepes 10, EGTA 10, MgATP 1.

Compounds were dissolved as stock solutions (20 mM) in DMSO. They were diluted to the final concentrations in the external solution.

Results

The compounds of this invention are able to block $Na^+$ currents in ND7/23 cells. The results obtained with 2-[2-(3-pentyloxyphenyl)-ethylamino]-N,N-dimethylacetamide hydrochloride NW-3525 and 2-[2-(3-butoxy-2-fluorophenyl)-ethylamino]-N,N-diethylacetamide, representative compounds of the chemical class of this invention, compared with our standard ralfinamide, are reported in Table 4.

TABLE 4

| COMPOUND | $IC_{50}$ resting (Kr) (μM) | $IC_{50}$ depolarized (μM) | Ki |
|---|---|---|---|
| 2-[2-(3-Pentyloxyphenyl)-ethylamino]-N,N-dimethylacetamide hydrochloride | 2.9 | 0.7 | 0.5 |
| 2-[2-(3-Butoxy-2-fluorophenyl)-ethylamino]-N,N-dimethylacetamide | 13 | 1.7 | 1 |
| (S)-(+)-2-[4-(2-Fluorobenzyloxy)-benzylamino]-propanamide (ralfinamide)* | 149.0 | 15.0 | 8.3 |

*as the salt with methanesulfonic acid

Data expressed as $IC_{50}$ value at μM concentration, as well as the affinity for the inactivated state (Ki) demonstrate that the two compounds of this invention is are a very potent and voltage dependent sodium channel blockers.

Example 15

In Vitro MAO-B Enzyme Activity Assay

Membrane Preparation (Crude Mitochondrial Fraction)

Male Wistar rats (Harlan, Italy weighing 175-200 g) were sacrificed under light anaesthesia and brains were rapidly removed and homogenized in 8 volumes of ice-cold 0.32 M sucrose buffer containing 0.1 M EDTA, pH 7.4. The crude homogenate was centrifuged at 2220 rpm for 10 minutes and the supernatant recovered. The pellet was homogenized and centrifuged again. The two supernatants were pooled and centrifuged at 9250 rpm for 10 minutes at +4° C. The pellet was resuspended in fresh buffer and centrifuged at 11250 rpm for 10 minutes at +4° C. The resulting pellet was stored at −80° C.

In Vitro Enzyme Activity Assay

The enzyme activity was assessed with a radioenzymatic assay using the substrate $^{14}$C-phenylethylamine (PEA) specific for MAO-B.

The mitochondrial pellet (500 µg protein) was resuspended in 0.1 M phosphate buffer (pH 7.4). 200 µl of the suspension were added to a 50 µl solution of the test compound or buffer, and incubated for 30 min at 37° C. (preincubation) then the substrate (50 µl) was added. The incubation was carried out for 10 minutes at 37° C. ($^{14}$C-PEA, 0.5 µM).

The reaction was stopped by adding 0.2 ml of perchloric acid. After centrifugation, the deaminated metabolites were extracted with 3 ml of toluene and the radioactive organic phase containing the neutral and/or acidic metabolites formed as a result of MAO-B activity was measured by liquid scintillation spectrometry at 90% efficiency.

The MAO-B activity was expressed as nmoles of substrate transformed/mg protein/min.

Compounds representative of the entire chemical class of this invention don't show MAO-B inhibition, at relevant concentrations, as reported in Table 5 as $IC_{50}$ values (the concentration of the compound able to inhibit by 50% the MAO-B enzyme activity).

As a matter of fact a significative MAO-B inhibition is considered when the $IC_{50}$ values are in the sub-micromolar range such as our standards safinamide and ralfinamide.

TABLE 5

| Compound | MAO-B $IC_{50}$ µM |
| --- | --- |
| 2-[2-(3-Butoxyphenyl)-ethylamino]-N-methylacetamide | 110 |
| 2-[2-(3-Butoxyphenyl)-ethylamino]-N,N-dimethylacetamide hydrochloride | 231 |
| 2-[2-(3-Butoxy-2,6-difluorophenyl)-ethylamino]-N,N-dimethylacetamide hydrochloride | >300 |
| 2-[2-(3-Butoxy-4-methoxyphenyl)-ethylamino]-N,N-dimethylacetamide | >300 |
| 2-[2-(3-Butoxyphenyl)-ethylamino]-N,N-dimethylpropanamide hydrochloride | >300 |
| (S)-(+)-2-[4-(3-Fluorobenzyloxy)-benzylamino]-propanamide (safinamide)* | 0.1 |
| (S)-(+)-2-[4-(2-Fluorobenzyloxy)-benzylamino]-propanamide (ralfinamide)* | 0.2 |

*as the salt with methanesulfonic acid

Example 16

Formalin Test

According to a modified protocol from Rosland et al. (Rosland J. H., Tjolsen A., Maehle B., Hole K. Pain (1990) 42: 235-242), mice were injected subcutaneously (s.c.) with 20 µl of 2.7% solution of formalin into the plantar surface of left hindpaw and placed immediately into clear PVC observation chambers (23×12×13 cm). Pain behaviour was quantified by counting the cumulative licking time (s) of the injected paw. Measurements were taken during the early phase (0-5 min) and late phase (20-40 min) after formalin injection (Tjolsen A., Berge O. G., Hunskaar S., Rosland J. H., Hole K. Pain (1992) 51:5-17).

The test compound was administered p.o. or s.c. 5-45 minutes before formalin injection in a volume of 10 ml/kg body weight to groups of 10 mice per dose. Control group was treated with vehicle.

The orally and subcutaneously administered compounds of the invention can be found active in this experimental model.

The results expressed as $ED_{50}$ value, obtained with one compound administered at 0.6-20 mg/kg p.o. and s.c., which is representative of the entire class of compounds of the invention, and reported in Table 6 demonstrates that this compound has a good analgesic activity.

TABLE 6

| Compound | $ED_{50}$ (mg/kg) p.o. |
| --- | --- |
| 2-[2-(3-Butoxyphenyl)-ethylamino]-N,N-dimethylacetamide hydrochloride | 14.9 |
| (S)-(+)-2-[4-(2-Fluorobenzyloxy)-benzylamino]-propanamide (ralfinamide)* | 29.3 |
| (S)-(+)-2-[4-(3-Fluorobenzyloxy)-benzylamino]-propanamide (safinamide)* | 69.4 |

*as the salt with methanesulfonic acid

Example 17

Spinal Nerve Ligation Model of Neuropathic Pain

Effects on neuropathic pain are tested in the Spinal Nerve Ligation model (SNL) (Kim S. H. and Chung J. M. (Pain (1992) 50: 355-363).

Animals: Adult male Wistar rats weighing 175-200 g were used. All animals were housed in groups of 8/10 in a temperature (22±0.5° C.) and relative-humidity (60-70%) controlled room on a 12-h light/dark cycle (lights on between a 6 a.m. to 6 p.m.) and allowed free access to water and standard diet for rodents.

Drugs: After measurement of a basal allodynic threshold, test compounds dissolved in distilled water was administered orally at the doses of 0.5-100 mg/kg in a volume of 2 ml/kg. Control rats were treated with vehicle.

Spinal nerve ligation: Neuropathy was produced according to a modified method described by Kim S. H. and Chung J. M. (Pain (1992) 50: 355-363). Briefly, the animals were anaesthetized with sodium thiopental 35 mg/kg i.p. (plus additional dose if needed) and after the exposure of the dorsal vertebral column from L4 to S2, the exposed L5 and L6 spinal nerves were tightly ligated with 4-0 silk suture, and the incision was closed. Rats were allowed to recover after surgery for about 5-14 days before testing.

Mechanical Allodynia: Mechanical allodynia thresholds were determined according to the method of Chaplan et al. (Chaplan S. R., Bach F. W., Pogrel J. W., Chung J. M. and Yaksh T. L. J. Neurosc. Method. (1994) 53: 55-63). Rats were placed in individual plastic boxes of 24×10×15 cm on a mesh metal floor and allowed to acclimate for about 30 min before testing. The paw withdrawal thresholds of the hind paws of the rats were determined in response to probing with 8 calibrated von Frey filaments (Stoelting, Wood Dale, Ill.) with logarithmically incremental stiffness ranging from 0.41 to 15 g (4 to 150 mN). Each filament was applied perpendicularly to the plantar surface of the ligated paw of rats. A maximal cut-off of 15 g was used. Withdrawal thresholds was determined by sequentially increasing and decreasing the stimulus strength ("up-down" method), analyzed by using a Dixon nonparametric test, and expressed as the mean withdrawal threshold (Dixon W. J. Am. Stat. Assoc. (1965) 60: 967-978). The mechanical allodynia thresholds both in the sham and operated animals was measured before (pre-drug) and at 15, 30, 60, 90, 120, 180, 240, 300, 360 and 420 min after p.o. treatment. A 24 h threshold was also measured in both treatment schedules.

The test was carried out between 9 a.m. and 6 p.m. The observers were blind to the experimental and treatment conditions.

Thermal hyperalgesia: Thermal hyperalgesia was assessed using the plantar test (Ugo Basile, Varese, Italy). The rats were placed in Plexiglas enclosures on a clear glass plate. With the rat standing relatively still, a radiant heat source beneath the glass floor was aimed at the plantar surface of the hind paw, and the withdrawal latency was measured. Before assessment of thermal hyperalgesia, the intensity of the radiant heat was adjusted to yield a baseline latency of about 20 seconds from naïve rats with the cutoff of automatically set at 30 seconds to avoid tissue damage.

Orally administered representative compounds of this invention were found active in this experimental model.

(FIG. 1: Effect of 2-[2-(3-butoxyphenyl)-ethylamino]-N,N-dimethylacetamide hydrochloride (NW-3509) orally administered in thermal hyperalgesia in SNL rats. ED50=10.58 mg/kg (6.7-16.6). Values represent the mean+SEM of 10 animals per group.)

Example 18

Complete Freund's Adjuvant Model of Chronic Inflammatory Pain

Monoarthritis was induced in rats (200 g weight) by an intra-plantar injection into the left hind paw of 100 µl of complete Freund's adjuvant (CFA, Sigma) containing heat-killed and dried *Mycobacterium tubercolosis* in a mixture of paraffin oil and an emulsifying agent, mannide monooleate. A group of naive rats were used as control. The CFA injection produced an area of localized oedema and inflammation starting from few h after injection, with a progressive reduction in the mechanical withdrawal threshold.

Each animal was allowed to develop the arthritis over a period of 8-9 days before testing. Mechanical Allodynia: Mechanical allodynia thresholds were determined according to the method of Chaplan et al. (Chaplan S. R., Bach F. W., Pogrel J. W., Chung J. M. and Yaksh T. L. J. Neurosc. Method. (1994) 53: 55-63). Rats were placed in individual plastic boxes of 24×10×15 cm on a mesh metal floor and allowed to acclimate for about 30 min before testing. The paw withdrawal thresholds of the hind paws of the rats were determined in response to probing with 8 calibrated von Frey filaments (Stoelting, Wood Dale, Ill.) with logarithmically incremental stiffness ranging from 0.41 to 15 g (4 to 150 mN). Each filament was applied perpendicularly to the plantar surface of the ligated paw of rats. A maximal cut-off of 15 g was used. Withdrawal thresholds was determined by sequentially increasing and decreasing the stimulus strength ("up-down" method), analyzed by using a Dixon nonparametric test, and expressed as the mean withdrawal threshold (Dixon W. J. Am. Stat. Assoc. (1965) 60: 967-978). The mechanical allodynia thresholds both in the sham and operated animals was measured before (pre-drug) and at 15, 30, 60, 90, 120, 180, 240, 300, 360 and 420 min after p.o. treatment. A 24 h threshold was also measured in both treatment schedules. The test was carried out between 9 a.m. and 6 p.m. The observers were blind to the experimental and treatment conditions.

Orally administered representative compounds of this invention were found active in this experimental model.

Example 19

Acetic Acid-Induced Visceral Pain Model in Mice

Visceral pain is still one of the most common forms of pain, which seeks medical care. Despite the conventional belief that visceral pain is a variant of somatic pain, it differs in neurological mechanisms and transmission pathways. Visceral pain is characterized by referral hyperalgesia and also it is not always linked to tissue injury.

The acetic acid-induced visceral pain model is widely used in experimental research to produce abdominal contractions (Korster R et al, Fed. Pro. (1959) 18: 412; Friese N et al., Life Sci. (1997) 60: 625-634) The model consists of intraperitoneal (i.p.) injection of an irritant that induces a syndrome called 'writhing', which consists of contractions of the abdomen, twisting and turning of the trunk, arching of the back and extension of the hind limbs.

Animals and procedure: Male CD1 mice weighing 25-33 g were used. Each treated group was allowed 30 min to habituate to laboratory surroundings in individual polypropylene transparent boxes. The visceral pain was scored by counting the number of writhes for 10 min after i.p. injection of 0.6% acetic acid (10 ml/kg of body weight). The number of writhes after acetic acid administration were evaluated. Both complete body stretching (complete writhe) or partial stretching with a clear contracting of the abdomen (partial writhe) were counted. Separate groups of 10 mice each were administered orally with vehicle (10 ml/kg), or different doses of the tested compound dissolved in vehicle (10 ml/kg), 5 min before acetic acid injection. Data are expressed as the mean number of writhes during the 10 min observation period.

Orally administered representative compounds of this invention were found active in this experimental model reducing the number of writhes induced by acetic acid.

(FIG. 2: Effect of 2-[2-(3-butoxyphenyl)ethylamino]-N,N-dimethylacetamide hydrochloride (NW-3509) orally administered at 20 mg/Kg p.o. in acetic acid induced visceral pain test. *p<0.01 vs. vehicle t-test. Values represent the mean+SEM of n=10 animals per group. *p<0.01 Dunnet's test.)

Example 20

Maximal Electroshock Test (MES) in Mice

The maximal electroshock test (MES) is used commonly in the screening of anti-epileptic drugs in rodent models.

Animals and Apparatus: Male CD1 mice weighing 25 g were used. The procedure described by White et al. (White H. S., Woodhead J. H., Franklin M. R., Swinyard E. A., and Wolf H. H. Antiepileptic Drugs (1995) 4th ed: 99-110, Raven Press, Ltd., New York) was followed. An Ugo Basile electroconvulsive generator (Model ECT UNIT 7801) was used to deliver an electrical stimulus sufficient to produce a hindlimb tonic extensor response in at least 97% of control animals. The stimulus was delivered intra-aurally through clip electrodes in mice (0.7 s of a 40 mA shock, with a pulse train of 80 Hz having a pulse duration of 0.4 ms). The acute effect of compounds administered intraperitoneally (i.p.), subcutaneously (s.c.), intravenously (i.v.) or orally (p.o.) 5-120 minutes before MES induction were examined and compared with a vehicle control group. Ten mice were studied per group. Complete suppression of the hindlimb tonic extensor component of seizures was taken as evidence of anticonvulsant activity.

The compounds of the invention were administered p.o. or i.v., at the doses of 0.1-100 mg/kg.

The results, expressed as ED50 values obtained with some compounds representative of the entire chemical class of the invention, are reported in Table 7 and in Table 8, demonstrate that these compounds are active as anticonvulsant drugs.

TABLE 7

| Compound | % protection 10 mg/kg p.o. | $ED_{50}$ (mg/kg p.o.) |
| --- | --- | --- |
| 2-[2-(3-Butoxyphenyl)-ethylamino]-N,N-dimethylacetamide hydrochloride | 100 | 4.3 |
| 2-[2-(3-Butoxyphenyl)-ethylamino]-N-methylacetamide hydrochloride | 30 | 12.1 |
| 2-[2-(3-Butoxy-2,6-difluorophenyl)-ethylamino]-N,N-dimethylacetamide hydrochloride | 100 | 2.0 |
| 2-[2-(3-Pentyloxyphenyl)-ethylamino]-N,N-dimethylacetamide hydrochloride | 100 | 2.8 |
| 2-[2-(3-Butoxy-4-methylphenyl)-ethylamino]-N,N-dimethylacetamide | 40 | n.d. |
| 2-[2-(3-Butoxyphenyl)-ethylamino]-N,N-dimethylpropanamide hydrochloride | 60 | 6.5 |
| 2-[2-(3-Hexyloxyphenyl)-ethylamino]-N,N-dimethylacetamide hydrochloride | 100 | 4.6 |

TABLE 8

| Compound | MES $ED_{50}$ mg/kg i.v. |
| --- | --- |
| 2-[2-(3-Butoxyphenyl)-ethylamino]-N,N-dimethylacetamide hydrochloride | 0.2 |
| (S)-(+)-2-[4-(2-Fluorobenzyloxy)-benzylamino]-propanamide (ralfinamide)* | 2.7 |
| (S)-(+)-2-[4-(3-Fluorobenzyloxy)-benzylamino]-propanamide (safinamide)* | 4.0 |

*as the salt with methanesulfonic acid

Example 21

Amphetamine and Chlordiazepoxide-Induced Hyperlocomotion in Mice

In this model, mice are treated with a mixture of d-amphetamine plus an anxiolytic dose of the benzodiazepine, chlordiazepoxide (Rushton R, Steinberg H. Combined effects of chlordiazepoxide and d-amphetamine on activity of rats in an unfamiliar environment. Nature 1966; 211: 1312-3; R. Arban, G. Maraia, K. Brackenborough, L. Winyard, A. Wilson, P. Gerrard, C. Large, Evaluation of the effects of lamotrigine, valproate and carbamazepine in a rodent model of mania Behavioural Brain Research, 158: 123-132). The model has been claimed to mimic some aspects of mania in bipolar disorder Importantly, the hyperactivity induced by the mixture of d-amphetamine and chlordiazepoxide could be prevented by prior administration of the established mood stabilizer, lithium, as well as other mood stabilizers drugs (e.g. magnesium valproate and carbamazepine). Therefore, this model has face and predictive validity as a model of bipolar disorder and represents a valuable tool to determine, if a test compound could be a potential mood stabilizer drug candidate.

Amphetamine (AMP) (2.5 mg/kg) plus chlordiazepoxide hydrochloride (CDZ) (3 mg/kg/ip) were administered to male Albino Swiss mice (25-32 g) in a volume of 10 ml/kg. The locomotor activity was recorded using Opto-M3 System (Columbus Instruments) which is multi-channel activity monitor. Opto-M3 system has 10 infrared emitters and respective amount of receivers (0.5" beam spacing), attached to the PC computer and calculating both ambulatory activity and total counts. Thus the system differentiates forward locomotion (ambulation) from stereotyped like movement (total counts). Mice were pretreated with the test compound (0.5-20 mg/kg) and 10 min later, with AMP (2.5 mg/kg) or AMP jointly with CDZ (3 mg/kg). After successive 30 min the mice were treated again with the same dose of the test compound and were placed individually in the motor activity cages. The locomotor activity (ambulation and total activity count) was evaluated for 30 min Each group consisted of 8-10 mice.

Statistical analysis: the data were evaluated by an analysis of variance (ANOVA), followed, when appropriate, by individual comparison with the control using Dunnett's test.

Results show that amphetamine and amphetamine-chlordiazepoxide (CDZ) administration induced a significant increase in locomotor activity.

Orally administered representative compounds of this invention were found active in this experimental model decreasing amphetamine and amphetamine-chlordiazepoxide induced hyperactivity.

Figure 3:
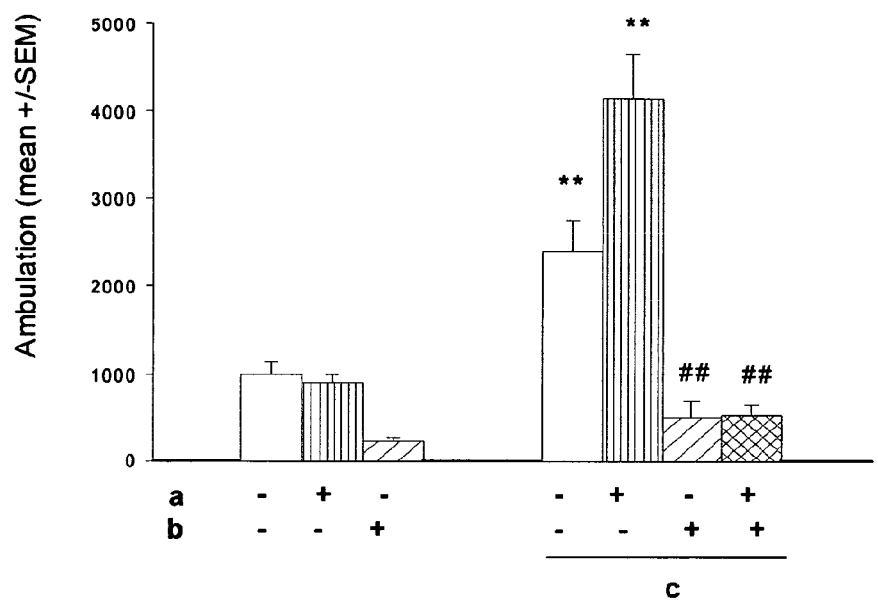
FIG. 3 provides results for antimania activity as measured using a mouse model having amphetamine and chlordiazepoxide-induced hyperlocomotion, further described in Example 21.

(FIG. 3: Ambulation over 30 min.

a) chlordiazepoxide (3.0 mg/Kg ip); b) 2-[2-(3-butoxyphenyl)ethylamino]-N,N-dimethylacetamide hydrochloride (NW-3509) (20.0 mg/Kg po); c) amphetamine (2.5 mg/kg i.p.).

Amphetamine alone and the mixture amphetamine+chlordiazepoxide significantly increased locomotor activity **$p<0.001$ Dunnet's test vs. vehicle.

2-[2-(3-Butoxyphenyl)ethylamino]-N,N-dimethylacetamide hydrochloride (NW-3509) reduced hyperactivity induced by both amphetamine alone and by the mixture of amphetamine and chlordiazepoxide in a statistical significant way ##$p<0.001$ Dunnet's test vs. amphetamine or amphetamine+chlordiazepoxide. Data represent the mean+SEM of n=10 mice per group.)

Example 22

Morris Water Maze Test (Amnesia Induced by Scopolamine in Rat)

The method which detects antiamnesic activity, follows that described by Morris (*Learn. Motiv.*, 12, 239-260, 1981). The Morris Maze consists of a circular water tank (Diameter=150 cm) filled with water and maintained at 26-28° C. with an escape platform (Diameter=15 cm) 18 cm from the perimeter and always in the same position 1.5 cm beneath the surface of the water. The water is made opaque by addition of a non-toxic coloring agent (e.g. milk powder) rendering the platform invisible.

The animals are given 4 training sessions over 4 consecutive days (Day 1 to Day 4). Each training session consists of 4 trials in the Morris Maze, each separated by 1 minute. For each trial the animal is placed in the maze at one of four starting points equally distributed around the maze and allowed to find the escape platform. The animal is left on the escape platform for 60 seconds before being returned to its home cage. If the animal does not find the platform within 120 seconds the experimenter removes it from the water and places it on the platform for 60 seconds before replacing it in its home cage. During the 4 trials the animals start the maze once from each starting point in a randomly determined order per animal.

The trials are video-recorded and the behaviour of animals is analyzed using a video-tracking system (Panlab:

SMART). The principal measure taken is the escape latency at each trial. Additional measures are the swim speed and distance travelled.

Scopolamine-treated animals (0.5 mg/kg i.p., administered 30 minutes before each session) show amnesia in this task as indicated by the failure to reduce their escape latencies from trial to trial and from session to session. A probe test will be performed on Day 5. The platform is removed from the maze and the animal allowed to swim freely in the maze for 60 seconds. The principal measure taken is the time spent in the target quadrant (i.e. that previously containing the platform), which is compared with the time spent in the other quadrants and with the value expected by chance (i.e. 25% of probe test duration). Twelve scopolamine-treated rats are studied per group. The experiment also includes a normal control group receiving saline instead of scopolamine. The test substance is evaluated at 3 doses, administered p.o. 5-60 minutes before the each training session and the probe trial, i.e. 30 minutes before scopolamine, and compared with a vehicle control group. The experiment will therefore include 5 groups.

Data are analyzed by comparing treated groups with scopolamine control using unpaired Student's t tests.

Orally administered representative compounds of this invention were found active in this experimental model.

Example 23

Cognition Model-Novel Object Recognition Test

The object recognition test consists of a sample trial and a choice trial separated by an inter-trial interval (ITI). On the sample trial, two identical objects are presented. On the choice trial, one of the objects presented in sample trial (termed as familiar objects) is replaced by a new object. Rats are able to discriminate between the familiar object and the new object when the ITI is 1 h or less, but not with a 24 h ITI (Deschaux O, et al, 1997, Neurosci. Lett. 222, 159-162; Ennaceur A, et al, 1989., Behav. Brain Res. 33, 197-207; Puma C, Bizot J C, 1998, Neurosci. Lett. 248, 183-186.). Therefore, the object recognition task with a 1 h ITI allows to detect the amnesic effect of a drug and whether this amnesic effect is reduced by another drug. The object recognition test with a 24 h ITI allows to detect a drug-induced enhancement of memory. Numerous studies have been conducted in order to assess memory effects of drugs. For example, past studies demonstrated that nicotine improves memory in the 24-h ITI condition and reduces scopolamine-induced amnesia in the 1-h ITI condition.

Methods: The object recognition task is performed as described in Bizot J C, et al, 2005 Prog Neuropsychopharmacol Biol Psychiatry. 29:928-935

Subjects: Naive 8-week old male Wistar rats were used

Apparatus: The apparatus of the object recognition task is an open box made of grey opaque Plexiglas (40 cm L, 40 cm W, 40 cm H). The objects to be discriminated (3.5 cm L, 6 cm H) differ in both color and shape. They are a white door button round shape and a grey door button star shape. Apparently, they have no natural significance for rats and they had never been associated with reinforcement. In order to rule out the possibility of scent traces left on the objects and therefore the dependency of the recognition capacity of rats on the olfactory cue, the objects and the ground of the box are washed with clear water and dried between each trial. A video camera is fixed to the ceiling above the box to monitor the animals' activity.

Experiments take place over 2 days (scopolamine-induced amnesia) or 3 days (natural forgetting). The test consists of a 15-min habituation trial (day 1), a 3-min sample trial (day 2) and a 3-min choice trial (day 2 or day 3).

Scopolamine-induced amnesia experiment. This experiment is conducted on rats randomly subdivided in different groups (n=12/group) which receive:
  control group: 1 intraperitoneal (IP) injection of saline 30 min before the test (sample trial) 1 per-os (PO) injection of saline 15 min before the test and.
  Scopolamine group: 1 IP injection of scopolamine (0.1 mg/kg) 30 min before the test and 1 PO injection of saline 15 min before the test (sample trial)
  Scopolamine+Nicotine group: 1 IP injection of scopolamine (0.1 mg/kg) 30 min before the test and 1 IP injection of nicotine (0.4 mg/kg) 20 min before the test (sample trial)
  Scopolamine+representative tested compound groups: 1 IP injection of scopolamine (0.1 mg/kg) 30 min before the test (sample trial) and 1 PO injection of different doses of the tested compound 15 min before the test (sample trial).

On Day 1 The rat is allowed to explore the apparatus for 15 min (Habituation trial). On day 2 the rat is placed in the apparatus with two identical objects presented in two corners of the box for 3 min (sample trial). After 1 hr the rat is placed in the apparatus with two objects; one of the objects presented in sample trial (termed as familiar objects) is replaced by a new object. (Choice trial).

Natural forgetting experiment: This experiment is conducted on rats randomly subdivided in different groups (n=12/group) which receive
  Control group: 1 intraperitoneal (IP) injection of saline 20 min before the test and 1 per-os (PO) injection of saline 15 min before the test.
  Nicotine group: 1 IP injection of nicotine (0.2 mg/kg) 20 min before the test and 1 PO injection of saline 15 min before the test.
  Representative tested compound group: 1 IP injection of saline 20 min before the test and 1 PO injection of tested compound at various doses 15 min before the test.

On Day 1 The rat is allowed to explore the apparatus for 15 min (Habituation trial). On day 2 the rat is placed in the apparatus with two identical objects presented in two corners of the box for 3 min (sample trial). Twenty four hours later (day 3) the rat is placed in the apparatus with two objects; one of the objects presented in sample trial (termed as familiar objects) is replaced by a new object.

Data: The basic measurement is the time spent by the rats in exploring the objects during the sample trial and during the choice trial. Object recognition task indices include the following parameters:
  The total exploration time in the sample trial,
  The total exploration time in the choice trial.
  The difference of exploration time between the new object and the familiar object in the choice trial (N−F).
  The discrimination index, that is 100×(N−F) divided by the total exploration time in the choice trial.
  Data are analysed by ANOVA and Student's t-test.

Orally administered representative compounds of this invention were found active in this experimental model reducing scopolamine-induced amnesia in the object recognition task with a 1-h inter trial interval (1 hr ITI) and improving memory in a natural forgetting situation, i.e. in the object recognition task with a 24 hours inter trial interval (24 hr ITI).

Example 24

Depression Test: Tail Suspension Test in the Mouse

Tail-suspension test is one of the so-called "behavioural despair" models and are used for the screening of antidepressant drugs. They are based on a common phenomenon: a normal animal submitted to a non-soluble aversive situation alternates between agitation and immobility. The reason of agitation is searching, it is highly energy consuming, while the purpose of immobility is energy conservation Animals after antidepressant treatment struggle more even in desperate situation, and they spend less time with immobility. Some aspects of neurotic depression can be studied with the aid of these models.

The present method detects antidepressant and anxiolytic activity and follows that described by Stem et al (*Psychopharmacology,* 85, 367-370, 1985). Rodents, suspended by the tail, rapidly become immobile. Antidepressants decrease the duration of immobility, whereas tranquillizing agents increase the duration of immobility. The behaviour of the animal is recorded during 6 minutes automatically using a computerized device (Itematic-TST) developed by Stem et al (*Prog. Neuropsychopharmacol. Exp. Psychiatry,* 11, 659-671, 1987). 6 mice are studied simultaneously. Two parameters are recorded:

- Duration of immobility: this parameter is analogous to that used in the "behavioural despair" test (*Arch. Int. Pharmacodyn. Ther.,* 229, 327-336, 1977).
- Power of movements: this parameter, based on the energy expended by the animal, is independent of the duration of activity.

10 mice are studied per group. The test is not performed blind but the randomization schedule generated by the Itematic-TST ensures a homogeneous distribution of the treatments both in time and in the position of each animal in the apparatus. The test substance is evaluated at 3 doses, administered p.o. 5-60 minutes before the test, and compared with a vehicle control group. Imipramine (128 mg/kg p.o.) and diazepam (8 mg/kg p.o.), administered under the same experimental conditions, are used as reference substances.

The experiment therefore includes 6 groups. Data are analyzed by comparing treated groups with vehicle control using unpaired Student's t tests.

Orally administered representative compounds of this invention were found active in this experimental model.

Example 25

Cognitive Impairment in Schizophrenia Method

Cognitive impairment is often associated with schizophrenia and it has come to be recognized as a core element of the disorder, bearing on patient's recovery and re-integration into society.

Particular interest has recently attracted a pharmacological model of cognitive dysfunctions in schizophrenia, which is based on the effects of glutamate NMDA receptor antagonists such as phencyclidine (PCP) and ketamine (Javitt et al., *Am. J. Psychiatry,* 1991 October, 148(10), 1301-1308) which impair attention and increase "impulsivity" and "compulsive" perseveration in mice performing a complex task (Greco et al., Psychopharmacology (Berl) 2005 April 179(1), 68-76).

Materials and Methods

Animals:

Male DBA/2N mice (Charles River, Italy) were used. The mice weighed 25-30 g at the start of the experiments, and were housed under temperature-controlled conditions (21° C.) with a 12 h light 12 h dark cycle (light on 7:00 am-7:00 pm). Food (Rieper, Italy) was available ad libitum. The animals had two hours of access to water at the end of each day's testing.

The Five-Choice Serial Reaction Time Task Apparatus:

The test apparatus consisted of four 21.6×17.8×12.7 cm chambers (Med Associates Inc. USA), as previously described (Greco et al., Psychofarmacology (Berl), 2005 April 179(1), 68-76). Stimuli and recording of responses, were managed by a SmartCtrl™ Package 8 In/16 Out (Med Associates Inc. USA) with additional interfacing by MED-PC for Windows (Med Associates Inc. USA). The running program for the 5-CSRT task was custom-written.

Behavioural Procedures: Habituation to Liquid Reinforcer and Nose-Poking in the Holes.

Mice were handled for one week and their body weight recorded. They were then water-deprived by allowing them 2-h access to water in the early evening until their body weight had stabilised (8 days). Then, over the next two days the mice were habituated in their home cages to the reinforcer (10% sucrose solution) used afterwards in the operant procedures. On the following two days mice were habituated to the operant boxes. During this stage, 10% sucrose solution was available in a small bowl placed below the receptacle hole of the box. First, mice had to learn that every 5 sec the liquid reward was available in a small cup in the receptacle hole. During this period head entries were recorded. During the next period, mice were trained to poke their noses into the illuminated holes Immediately after a poke in the water receptacle a LED at the rear of one of the holes was turned on. A nose-poke in the lighted hole extinguished the light stimulus and the liquid dipper provided a 0.01 mL liquid reward in the receptacle hole. Any response in one of the other four holes had no consequence and was not recorded. The light stimulus was presented in all five holes in random order. A mouse was switched to the 5-CSRT task after it had completed at least 50 rewarded nose-poke trials in one 30-min session.

The Five-Choice Serial Reaction Time Task.

The start of the session was signalled by illumination of the house-light and the delivery of a 0.01 mL liquid reward. Nose poking in the receptacle hole began the first trial. After a fixed delay (the inter-trial interval, ITI), the LED at the rear of one of the holes came on for a short period. The LED stimulus was presented the same number of times in each hole during a complete session, with the order of presentation randomised by the computer. While the light was on, and for a short period afterwards (the limited hold), responses in the hole that was illuminated (correct response) resulted in the liquid reward. Responses in the holes that had not been illuminated (incorrect responses) or failure to respond within the limited hold (omissions) caused the house-lights to be turned off for a short period (time out). Responses in the holes while the house-light was off restarted the time out. After the delivery of the liquid reward, or at the end of time out, the mouse started the next trial by poking its nose into the receptacle hole. Responses made in the holes after a correct response (perseverative responses), or after the end of time out before nose-poking into the receptacle hole, resulted in a period of time out. Responses in the holes during the ITI (anticipatory responses) also resulted in a period of time out. After anticipatory responses a nose-poke into the receptacle hole restarted the current trial. Each daily session consisted of 100 trials or 30 min of testing, whichever was completed sooner, after which all lights were turned off and further responses had no effect. In the first session of the test schedule, the stimulus and limited hold each lasted 1 min and, depending on individual performance, they were progressively reduced to 1 sec. The stimulus duration was reduced in the following sequence: 60, 30, 10, 5, 2.5, 2, 1.5 and 1 sec (baseline). The ITI and time out both lasted 2 sec during the first session and the ITI was raised to 5 sec in subsequent sessions; time out was not changed. Throughout the whole period of training and experiments each mouse had one session per day on a 5-CSRT task.

Drugs and Treatment Schedules.

The test compound is dissolved in water and is administered intraperitoneally (i.p.) at the dose of 10 mg/kg. Five minutes after the treatment mice were injected with vehicle (saline) or PCP (1.5 mg/kg) and 10 min later they started the test session. In each experiment the various combination of the test compound with vehicle or PCP are administered according to a Latin-square design. At least 48 h are left between the drug testing days. During these intervening days the mice are tested on the 5-CSRT task to re-establish baseline performance and to check for any residual effects of drugs.

Statistical Analysis:

the main dependent variables selected for analysis are: (a) the percentage of correct responses (total correct responses/total correct+total incorrect responses×100); (b) percentage of omissions (total omissions/total correct responses+total incorrect responses+total omissions×100); (c) the number of anticipatory responses in the holes during the ITI; (d) the number of perseverative responses in the holes after a correct response. Correct responses and omissions, as percentages, are transformed according to the formula 2 arcsin (SQRT (% X/100)), to normalize the distributions in accordance with the ANOVA model (Winer, 1971).

The effects of the test compound (n=12) on PCP induced deficits in the 5-CSRT task were analysed independently by a within subjects 2×2 ANOVA with factors Drug (test compound) and PCP. Subsequently the treatment group means are compared using a post-hoc Tukey-Kramer test. Statistical software (SAS Institute Inc., USA) was run on Micro VAX 3500 computer (Digital, USA).

PCP causes a profound effect on attentional performance of DBA/2N mice increasing anticipatory and perseverative responses.

Representative compounds of this invention, administered 10 mg/Kg i.p., reversed PCP-induced increase in anticipatory and perseverative responses, supporting the use of this kind of compounds for the treatment of psychiatric disorders.

Example 26

Prepulse Inhibition of Startle in Mice and Rats

Prepulse inhibition (PPI) is a cross-species phenomenon (ie, it is present in mammals ranging from mice to humans), yet it is relatively absent among schizophrenic patients. The reduced ability to filter out among irrelevant auditory stimulation is a characteristic thought to contribute to certain manifestations of these conditions including inattention, distractibility, and cognitive deficits. The PPI procedure is used to assess the subject's ability to "gate" or filter environmental information. In the acoustic (startle model) of sensorimotor gating a weak acoustic stimulus (prepulse) decrease the reflexive flinching response (startle) produced by a second, more intense, stimulus (the pulse). Drugs like dizocilpine (MK-801) or amphetamine disrupt PPI and represent an animal model of schizophrenia. Antipsychotic drugs are able to prevent PPI deficit. The test is quite useful to screen potential antipsychotic drugs.

Similarly some strains of mice such as the DBA/J display a spontaneous impairment of PPI that can be reversed by antipsychotic drugs and are also used as animal model of schizophrenia.

PPI in rat: Wistar or Sprague-Dawley rats (weighing 200 to 300 g) or 3-week-old DBA/2J mice were used. The startle apparatus (San Diego Instruments, CA) consisted of 12 plastic transparent cages, placed individually in a sound-proof cabinets, equipped with a movable platform floor attached to a sensor recording vertical movements of the platform. Startle reaction was evoked by acoustic stimuli delivered by a loudspeaker suspended above the cages and connected to an acoustic generator. The transient force resulting from the movements of the platform evoked by the startle reaction was recorded with a PC computer during a recording window of 200 ms measured from the onset of the acoustic stimulus, digitalized and stored in the computer for further evaluation. The amplitude of the startle response was measured during the whole recording window (200 ms) and an average value of amplitude was taken for further evaluation. The control and treated rats were placed in the testing cages individually. After 5 min of habituation (background white noise, 65 dB), two types of acoustic stimuli were used in random order: acoustic stimulus alone [120 dB, 40 ms, (P)] or the stimulus proceeded by a prepulse [75 dB, 20 ms (PP)] applied 100 ms before the stimulus. During each experimental session 20 trials of each type were presented with interstimulus interval of 20 s. The amplitudes were averaged for each individual animal, separately for both types of trials (stimulus alone or stimulus preceded by the prepulse). The percent PPI was calculated with the following formula: 100−[(mean startle amplitude for prepulse+pulse trials/mean startle amplitude for pulse alone trials)×100] i.e. 100−(PP/P)×100. A high value of the calculated % PPI indicated that the prepulse inhibited the response to a pulse stimulus, whereas a low value indicated weaker inhibition by prepulse. Deficits of sensorimotor gating was induced by MK-801 (0.2 mg/kg) given ip 5 min before test or amphetamine (2.5 mg/kg) given sc 10 min before test. Orally administered representative compounds of this invention were found active in this experimental model, reversing PPI deficit induced by MK-801 (FIG. 4) or by amphetamine.

PPI in DBA mice: Male 3-week-old DBA/2J and C57BL/6J mice were used.

Detection of acoustic startle response and PPI was performed as described in Bortolato et al Psychopharmacology, 2007, October; 194(3): 361-9.

In each experiment, mice were assigned to receive either compounds of the invention or vehicle and were tested in the PPI session using a between-subjects design.

The percent PPI was calculated with the following formula: 100−[(mean startle amplitude for prepulse+pulse trials/mean startle amplitude for pulse alone trials)×100] i.e. 100−(PP/P)×100. The magnitude of the acoustic startle response was calculated as the average response to all of the pulse-alone trials, excluding the first and last blocks of five pulse-alone trials presented.

Orally administered representative compounds of this invention were found active in this experimental model reducing PPI deficit of BDA/2J mice.

(FIG. 4: Effect of 2-[2-(3-butoxyphenyl)ethylamino]-N,N-dimethylacetamide hydrochloride (NW-3509) in MK-801 PPI disruption in rats. Data are expressed as mean+SEM of n=10 animals. p<0.01 indicate statistically significant difference between vehicle and MK-801. *p<0.05 **p<0.01 indicate statistically significant differences between vehicle+MK-801 treated animals and animals treated with 2-[2-(3-butoxyphenyl)ethylamino]-N,N-dimethylacetamide hydrochloride (NW-3509).

Analysis of variance followed by Dunnet's test.)

Example 27

Paradoxical Sleep Deprivation in Rats

The psychopathological and neurobiological relationships between sleep and psychotic phenomena have been evidenced by a number of classical clinical observations and psychological reports. Schizophrenic patients exhibit severe insomnia, together with a number of structural alterations of sleep architecture, such as a reduction in REM sleep latency and duration, as well as a decrease in SWS (Slow Wave Sleep) time. Numerous studies have demonstrated that prolonged sleep deprivation is indeed conducive to a number of transient psychological disorders, including impaired verbal constructions, disorganized thought, depersonalization and perceptual changes, ranging from minor disturbances and abnormal bodily sensations to complex acoustic and visual hallucinations. Typically, these disorders are indistinguishable from psychotic phenomena, but are normally extinguished following a prolonged recuperative sleep. Several studies have documented that following a period of forced sleep deprivation, rats exhibit for a limited time a paradoxical array of behavioral changes, such as stereotyped behavior and hyperactivity. Moreover, sleep deprivation in rats enhances startle reaction and disrupts PPI, this effect is time-dependent and reversible by antipsychotic drugs (Gessa, G L et al. (1995) *European Neuropsychopharmacology* 5, 89-93). Such phenomena are commonly interpreted as relevant to psychosis, as they are also typically produced by psychotomimetic agents in rats. The model of sleep deprivation in rats can be considered a model of mania.

Animals: Sprague-Dawley rats (weighing 200 to 300 g) were used.

Methods: The procedure to induce paradoxical sleep deprivation (SD) in rats is based on the platform method (modified from Jouvet, et al (1964). *Journal of Physiology (Paris)*, 56, 381). Rats were kept on a small Plexiglas platform (7 cm in diameter) within a deep tank filled with water. Each platform was surrounded by water up to 1 cm, beneath the surface. Chow pellets and water bottles were located on a grid on the top of the tank. During the whole SD study, the temperature of the experimental room and the water inside the tank were maintained at 23±1° C. Control rats are placed in the experimental room, either in their home cages or on water tanks equivalent to those used for SD, but with a 12 cm-diameter platform, which allows them to reach REM sleep without falling into the water. At the end of the SD period (72 hr), rats were immediately dried out and placed either in the startle chambers (for PPI measurement) or in the activity cages (hyperactivity) for behavioral testing. The water in the tank was changed daily throughout the SD period. Control rats were maintained in the same room as the sleep-deprived rats for the duration of their SD. Compounds to be tested were given before PPI or behavioural testing.

Data Analysis: For each animal, the mean startle amplitudes for the first and the second halves of the second period of the session (blocks, six pulse-alone trials each) were analyzed with a two-way or three-way analysis of variance (ANOVA), with pretreatment (where present) treatment as between-subjects factors and blocks as repeated measures. The percent PPI was calculated with the following formula: 100−[(mean startle amplitude for prepulse+pulse trials/mean startle amplitude for pulse alone trials)×100] i.e. 100−(PP/P)×100 and analyzed in multifactor ANOVAs (with specific design and comparisons noted below for each experiment) with the different combinations of injections for pretreatment and treatment as between-subjects factors and trial types as repeated measures. Post hoc analyses were performed using Tukey's test. Locomotor activity data were analysed using the one- or two-way analysis of variance (ANOVA) for repeated measures when appropriate, followed by Tukey's test as post-hoc tests.

Orally or intraperitoneally or subcutaneously administered representative compounds of this invention were found active in this experimental model reducing PPI deficit and hyperactivity induced by sleep deprivation.

Example 28

Cocaine-Induced Behavioural Sensitization Test

Drug addiction is a pathological behaviour characterized by compulsive drug seeking and intake. One animal model of these behavioural changes is the long-lasting increase in locomotor activity induced by repeated administration of psychostimulant drugs in rodents (Robinson T. E. and Berridge K. C. Brain Res. Brain Res. Rev. (1993) 18, 247-91) known as drug-induced behavioural sensitization. The effect of test compounds were evaluated in a model of cocaine-induced behavioural sensitization in rat.

Locomotor activity apparatus: Male Wistar rats weighing 200-250 g upon arrival were used. Locomotor activity was measured in sixteen identical metal wire hanging cages each measuring 36 cm (L)×25 cm (W)×20 cm (H). Each cage contained two sets of infrared emitter-detector photocells positioned along the long axis 1 cm above the grid floor and 8 cm from the front and back of the cage. Background noise was provided by a white noise generator. Movement within the cages produced photocell interruptions, which were automatically recorded by an IBM-compatible computer.

Sensitization procedure and treatment: Animals were habituated to the locomotor activity chambers for 2-3 consecutive days before the experiment. Rats received 5 daily i.p. injections of cocaine (15 mg/kg) or saline and either the test compound (0.1-100 mg/kg) or its vehicle and locomotor activity was recorded for 3 h. Ten days after the last injection of cocaine or saline (day 15), the animals were challenged with 15 mg/kg of cocaine in absence of the test compound and locomotor activity was again monitored for 3 h.

By the fifth day of treatment with cocaine, animals pretreated i.p. with vehicle showed an increased locomotor response (20% higher then the first day, p<0.05). Ten days after the last injection of cocaine or saline, the animals were challenged with 15 mg/kg of cocaine in absence of the test compound and locomotor activity was again monitored for 3 h. The rats previously treated with cocaine and that had not received the test compound are expected to show an increased locomotor activity response to cocaine (30% higher then first day, p<0.05). If the rats that had been pretreated with the test compound during the 5 day-cocaine treatment did not show an increase in locomotor activity the test compound is considered to have an effect in preventing psychostimulant drugs addiction. (Koob G. F., Sanna P. P., Bloom F. E. Neuron (1998) 21: 467-476; Robinson T. E., Berridge K. C. Brain Res Brain Res Rev (1993) 18: 247-291)

Statistical analysis: Data (total number of beam breaks in 3 hours) were analyzed using a two way ANOVA with repeated measures on one factor including the four experimental groups (i.e., saline/vehicle, saline/test compound, cocaine/vehicle and cocaine/test compound) and two time points (day 1 and day 5) followed by a simple effects analysis. A second two way ANOVA with repeated measures on one factor was used to compare day 1 and the challenge day followed by a Newman-Keuls post hoc test.

Orally administered representative compounds of this invention were found active in this experimental model.

Example 29

Acute Bladder Irritation by Acetic Acid in Rats

Experiments were performed using adult anesthetized female Sprague Dawley rats (170-200 g). A catheter (PE-50) was inserted via a midline abdominal incision into the bladder through the bladder dome, and then intravescical pressure was measured to monitor bladder activity during continuous infusion of 0.15% acetic acid. Continuous intravescical infusion of acetic acid irritates the bladder and reduces the intercontraction intervals (ICI) in anesthetized rats. ICIs, maximal contraction pressure, and pressure thresholds inducing reflex bladder contraction were measured before and after intravescical infusion of acetic acid in rats treated with compounds of the invention.

Intraperitoneally or intravenously administered representative compounds of this invention were found active in this experimental model.

Example 30

Intermediate Bladder Irritation by Cyclophosphamide (CYP) in Rats

Experiments were performed using both adult awake and anesthetized female Sprague Dawley rats (170-200 g). Chemical cystitis was induced by CYP, which is metabolized to acrolein, an irritant eliminated in the urine. CYP (150 mg/kg/i.p.) was administered one day before the experiment. Pre-treatment with CYP causes bladder irritation and very frequent voidings with an ICI of about 150-200 seconds between voids.

Intraperitoneally or intravenously administered representative compounds of this invention increased the ICI in both awake and anesthetized rats used in this experimental model.

Example 31

Migraine Test in Rats

Animals and surgery: Male Wistar rats (250-350 g) were anesthetized with sodium pentobarbital (50 mg/kg i.p.) dissolved in saline.

The trachea and left femoral artery were cannulated for artificial ventilation (55 strokes/min) and for measurement of mean blood pressure (MBP) respectively. The femoral vein was cannulated for the intravenous administration of test agents.

Body temperature was maintained at 37-38° C. by automatic control of a heating pad. Animals were placed in a stereotaxic frame and a longitudinal incision was made in the scalp. A burr hole was drilled in the skull and a stainless steel bipolar electrode (Plastic One MS 306) was lowered into left ophthalmic branch of the trigeminal ganglion (3.8 mm dorsal to bregma, 2.5 mm lateral from the midline and 9.5 mm below the dural surface) and secured with dental cement. Correct placement of the electrode was confirmed by a brief electrical stimulation, which cause movement of the jaw due to activation of the trigeminal fiber. Following removal of the brain, the correct position of the electrode into the fiber, was visually checked at the end of each experiment.

A second hole was drilled ipsilateral of the electrode (1.5 mm rostral to bregma, and 1.5 mm lateral from the sagittal suture) and a needle probe (tip diameter 0.8 mm) of a laser doppler flowmeter was fixed pointing with its tip onto a branch of the middle cerebral artery (MCA) and Cerebral Blood Flow (CBF) change recorded on-line by the PeriFlux 4001 Laser Doppler system.

Artefacts of the laser Doppler reading during electrical stimulation of the trigeminal ganglion due to muscular movements were prevented by a bolus of i.v. injection of the neuromuscular blocker pancuronium bromide (0.6 mg/kg i.v.).

Anaesthesia and neuromuscular blockade were maintained all over the experiment with an infusion of sodium pentobarbital and pancuronium (12.5 mg/kg/h+2.4 mg/kg/h, respectively).

Experimental protocol: At the end of the surgery, a pause of thirty minutes was taken in order to stabilize the measured parameters.

Rest CBF was increased by electrical stimulation with rectangular pulse of 0.5 ms length, 1-10 Hz, 0.5-1 mA for periods of 30 s. After two averaged pre-drug stimulations, vehicle or drugs were administered.

Intravenously administered representative compounds of this invention reduced the increase in blood flow induced by trigeminal stimulation.

The invention claimed is:
1. A method for modulating voltage gated sodium and/or calcium channels, comprising the step of administering to a patient in need thereof an effective amount of a compound of formula (I):

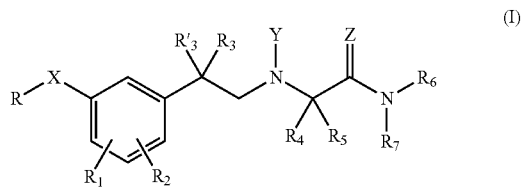

wherein:
X is —O—;
Y is hydrogen, —OH or —O($C_1$-$C_4$)alkyl;
Z is =O or =S;
R is —($C_3$-$C_{10}$)alkyl; ω-trifluoro($C_3$-$C_{10}$)alkyl;
$R_1$ and $R_2$ are, independently, hydrogen, hydroxy, ($C_1$-$C_8$)alkoxy, ($C_1$-$C_8$) alkylthio, halo, trifluoromethyl or 2,2,2-trifluoroethyl; or one of $R_1$ and $R_2$ is ortho to R—X— and taken together with the same R—X—, represents a

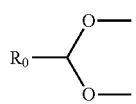

group where $R_0$ is —$(C_2$-$C_9)$alkyl;

$R_3$ and $R'_3$ are, independently, hydrogen or —$(C_1$-$C_4)$alkyl;

$R_4$ and $R_5$ are, independently, hydrogen or —$(C_1$-$C_4)$alkyl; or $R_4$ is hydrogen and $R_5$ is —$CH_2$—OH, —$CH_2$—O—$(C_1$-$C_6)$alkyl, —$CH(CH_3)$—OH, —$(CH_2)_2$—S—$CH_3$, benzyl or 4-hydroxybenzyl; or $R_4$ and $R_5$, taken together with the adjacent carbon atom, form a $(C_3$-$C_6)$cycloalkyl residue;

$R_6$ and $R_7$ are, independently, hydrogen or —$(C_1$-$C_6)$alkyl; or taken together with the adjacent nitrogen atom form a 5- or 6-membered monocyclic saturated heterocycle, optionally containing —O—, —S— or —$NR_8$—, wherein $R_8$ is hydrogen or $(C_1$-$C_6)$alkyl;

its pharmaceutically acceptable salts and the isolated optical isomers or mixtures of optical isomers of the compound and their pharmaceutically acceptable salts, wherein a disease treatable by such modulation is a gastrointestinal disorder.

2. The method of claim 1, wherein said gastrointestinal disorder is caused by a dysfunction of a voltage-gated sodium channel.

3. The method of claim 1, wherein said gastrointestinal disorder is caused by a dysfunction of a voltage-gated calcium channel.

4. The method of claim 1, wherein said patient is sensitive to unwanted side effects of MAO inhibitory effects.

5. The method of claim 1, wherein the compound is administered with at least one other therapeutic agent.

6. The method of claim 1, wherein the effective amount of the compound administered to the patient in need thereof (i) does not exhibit any MAO-inhibitory activity or (ii) exhibits a reduced MAO-inhibitory activity.

7. The method of claim 1, wherein the compound is 2-[2-(3-butoxyphenyl)-ethylamino]-N,N-dimethylacetamide or a pharmaceutically acceptable salt thereof.

8. The method of claim 1 wherein the gastrointestinal disorder is selected from the group consisting of ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, pylorospasm, nervous indigestion, spastic colon, spastic colitis, spastic bowel, intestinal neurosis, functional colitis, mucous colitis, laxative colitis, functional dyspepsia, atrophic gastritis, gastritis varialoforme, ulcerative colitis, peptic ulceration, pyresis, damage to the GI tract by *Helicobacter pylori*, gastroesophageal reflux disease, gastroparesis, such as diabetic gastroparesis, non-ulcerative dyspepsia (NUD); emesis, diarrhoea, and visceral inflammation.

* * * * *